(12) United States Patent
Lewin et al.

(10) Patent No.: US 6,225,291 B1
(45) Date of Patent: *May 1, 2001

(54) ROD OPSIN MRNA-SPECIFIC RIBOZYME COMPOSITIONS AND METHODS FOR THE TREATMENT OF RETINAL DISEASES

(75) Inventors: Alfred S. Lewin; William W. Hauswirth; Kimberly Drenser, all of Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/063,667

(22) Filed: Apr. 21, 1998

Related U.S. Application Data

(60) Provisional application No. 60/046,147, filed on May 9, 1997, and provisional application No. 60/044,492, filed on Apr. 21, 1997.

(51) Int. Cl.$^7$ .................... A61K 31/7105; A61K 31/711; C07H 21/00; C12N 15/09; C12P 19/34
(52) U.S. Cl. .................... 514/44; 435/91.31; 435/320.1; 435/375; 435/456; 536/23.1; 536/24.5
(58) Field of Search ........................... 435/6, 375, 320.1, 435/455, 456, 457, 91.31; 514/44; 536/23.1, 24.3, 24.31, 24.5

(56) References Cited

U.S. PATENT DOCUMENTS

| | | |
|---|---|---|
| 4,987,071 | 1/1991 | Cech et al. . |
| 5,037,746 | 8/1991 | Cech et al. . |
| 5,093,246 | 3/1992 | Cech et al. . |
| 5,116,742 | 5/1992 | Cech et al. . |
| 5,498,539 | 3/1996 | Harrison et al. . |
| 5,639,655 | 6/1997 | Thompson et al. . |
| 5,646,020 | 7/1997 | Swiggen et al. . |
| 5,646,031 | 7/1997 | DeYoung et al. . |

FOREIGN PATENT DOCUMENTS

| | | |
|---|---|---|
| 95/04142 | 2/1995 | (WO) . |
| 97/11169 | 3/1997 | (WO) . |
| 97/32024 | 9/1997 | (WO) . |
| 98/48009 | 10/1998 | (WO) . |
| 98/48027 | 10/1998 | (WO) . |

OTHER PUBLICATIONS

LaVail et al. Ribozyme rescue of photoreceptor cells in P23H transgenic rats: Long–term survival and late-stage therapy. Prepublished online as Proc Natl. Acad. Sci. USA Early Edition (Sep. 26, 2000) 10.1073/pnas210319397.*
Report and recommendations of the panel to assess the NIH investment in research on gene therapy. Orkin and Motulsky, co–chairs. National Institutes of Health, Dec. 1995.*
Crooke, S. T. Vitravene—Another piece in the Mosaic. Antisense and Nucleic Acid Drug Development 8: vii–viii, 1998.*
Gewirth et al. Facilitating oligonucleotide delivery: Helping antisense deliver on its promise. Proc. Natl. Acad. Sci. USA 93: 3161–3163, Apr. 1996.*
Lyngstadaas et al. A synthetic, chemically modified ribozyme eliminates amelogenin, the major translation product in developing mouse enamel in vivo. EMBO J. 14: 5224–5229, 1995.*
Stein, C. A. Keeping the biotechnology of antisense in context. Nat. Biotechnol. 17: 209, Mar. 1999.*
Stull et al. Antigene, ribozyme and aptamer nucleic acid drugs: Progress and prospects. Pharm. Res. 12: 465–483, Apr. 1985.*
Christoffersen et al. Ribozymes as human therapeutic agents. J. Med. Chem. 38: 2023–2037, Jun. 1995.*
Alfione et al., "In vivo model of adeno–associated virus vector persistence and rescue," *Journal of Virology*, 70:3235–3241, 1996.
Altschuler et al., "A method for generating transcripts defined with 5' and 3' termini by autolytic processing," *Gene*, 122:85–90, 1992.
Al–Ubaidi et al., "Photoreceptor degeneration induced by the expression of simian virus 40 large tumor antigen in the retina of transgenic mice," *Proc.Natl. Acad. Sci. USA*, 89:1194–1198, 1992.
Cech, "Self–splicing of Group I introns," *Annu. Rev. Biochem*, 59:543–568, 1990.
Chakravathy et al., "Nitric oxide synthase activity and expression in retinal capillary endothelial cells and pericytes," *Curr. Eye Res.*, 14(4):285–294, 1995.
Chen et al., "The human blue opsin promoter directs transgene expression in short–wave cones and bipolar cells in the mouse retina," *Proc. Natl. Acad. Sci. USA*, 91(7):2611–2615, 1994.
Chiu et al., "A sequence upstream of the mouse blue visual pigment gene directs blue conespecific transgene expression in mouse retinas," *Visual Neuroscience*, 11(4):773–780, 1994.
Cipolla, Porter and Osol, "High glucose concentrations dilate cerebral arteries and diminish myogenic tone through an endothelial mechanism," *Stroke*, 28(2):405–411, 1997.
Cosentino et al., "High glucose increases nitric oxide synthase expression and superoxide anion generation in human aortic endothelial cells," *Circulation*, 96(1):25–28, 1997.
Crystal, "Transfer of genes to humans: early lessons and obstacles to success," *Science*, 270:404–410, 1995.
Daiger, Sullivan and Rodriguez, "Correlation of phenotype with genotype in inherited retinal degeneration," *Behavioral and Brain Sciences*, 18:452–467, 1995.

(List continued on next page.)

*Primary Examiner*—John L. LeGuyader
*Assistant Examiner*—Thomas G. Larson
(74) *Attorney, Agent, or Firm*—Williams, Morgan & Amerson, P.C.

(57) ABSTRACT

The subject invention provides materials and methods for efficient, specific reduction or elimination of unwanted mRNA. These materials and methods can be used in therapies for retinal diseases. In one embodiment, ribozymes which degrade mutant mRNA are used to treat retinitis pigmentosa.

62 Claims, 7 Drawing Sheets

OTHER PUBLICATIONS

DesJardin and Hauswirth, "Developmentally important DNA elements within the bovine opsin upstream region," *Investigative Ophthalmology & Visual Science*, 37(1):154–165, 1996.

Drenser et al., "Ribozyme mediated degredation of the P23H and S334Ter mutant mRNAs associated with ADRP," *Investigative Opthalmology& Visual Science*, 38(4):S441, Abstract 2085, 1997 (Annual Mtg. Of the Association for Research in Vision and Opthalmology, Fort Lauderdale, Florida, USA, May 11–16, 1997).

Drenser et al., "Ribozyme mediated destruction of an messenger–RNA causing retinitis pigmentosis," *Investigative Ophthalmology& Visual Science*, 37(3):S10, Abstract 42, 1996.

Drenser et al., "Ribozyme–targeted destruction of RNA associated with autosomal–dominant retinitis pigmentosa," *Investigative Ophthalmology & Visual Science*, 39(5):681–689, 1998.

Flannery et al., "Efficient photoreceptor–targeted gene expression in vivo by recombinant adenoassociated virus," *Proc. Natl. Acad. Sci. USA*, 94(13):6916–6921, 1997.

Flotte et al., "Stable in vivo expression of the cystic fibrosis transmembrane conductance regulator with an adeno–associated virus vector," *Proc. Natl, Acad. Sci. USA*, 90(22):10613–10617, 1993.

Gade et al., "Nitric oxide mediates hyperglycemia–induced defective migration in cultured endothelial cells," *Journal of Vascular Surgery*, 26(2):319–326, 1997.

Goldstein, Ostwal and Roth, "Nitric oxide: a review of its role in retinal function and disease," *Vision Res.*, 36(18):2979–2994, 1996.

Hangai et al., "Inducible nitric oxide synthase in retinal ischemia–reperfusion injury," *Exp. Eye Res.*, 63(5):501–509, 1996.

Hauswirth et al., "Adeno–associated virus delivery of an opsin promoter driven reporter gene to the mouse and rabbit retina," *Gene Therapy*, 2(Supp. 1):S2, Abstract 6, 1995.

International Search Report dated Feb. 1, 1999 (PCT/US98/07968) (4300.011510).

International Search Report dated Feb. 16, 1999 (PCT/US98/08003) (4300.011410).

Kaplitt et al., "Long–term gene expression and phenotypic correction using adeno–associated virus vectors in the mammalian brain," *Nature Genetics*, 8:148–154, 1994.

Kessler et al., "Gene delivery to skeletal muscle results in sustained expression and systemic delivery of a therapeutic protein," Proc. Natl. Acad. Sci. USA, 93:14082–14087, 1996.

Kido et al., "Use of a retroviral vector with an internal opsin promoter to direct gene expression to retinal photoreceptor cells,", *Current Eye Research*, 15:833–844, 1996.

Koizumi, Kiroyuki and Eiko, "Ribozymes designed to inhibit transformation of NIH3T3 cells by the activated c–Ha–ras gene," *Gene*, 117:179–184, 1992.

Komatsu et al., "A new type of hairpin ribozyme consisting of three domains," *Biochemistry*, 36(32):9935–9940, 1997.

Lem et al., "Tissue–specific and developmental regulation of rod opsin chimeric genes in transgenic mice," *Neuron*, 6:201–210, 1991.

Lewin et al., "Ribozyme rescue of photoreceptor cells in a transgenic rat model of autosomal dominant retinitis pigmentosa," *Nature Medicine*, 4(8):967–971, 1998.

Li et al., "Cone–specific gene transfer and expression using human red/green opsin promoter in a recombinant AAV,", *IOVS*, 39(4):S721, 3311–B137, 1998.

Little and Lee, "Generation of a mammalian cell line deficient in glucose–regulated protein stress induction through targeted ribozyme driven by a stress–inducible promoter," *The Journal of Biological Chemistry*, 270(16):9526–9534, 1995.

Millington–Ward et al., "Strategems in vivo for gene therapies directed to dominant mutations," *Human Molecular Genetics*, 6(9):1415–1426, 1997.

Ojwang et al., "Inhibition of human immunodeficiency virus type 1 expression by a hairpin ribozyme," *Proc. Natl. Acad. Sci. USA*, 89:10802–10806, 1992.

Ostwald et al., "Effect of nitric oxide synthase inhibition on blood flow after retinal ischemia in cats," *Investigative Ophthalmology & Visual Science*, 36(12):2396–2403, 1995.

Raymond et al., "Expression of rod and cone visual pigments in goldfish and zebrafish: a rhodopsin–like gene is expressed in cones," *Neuron*, 10:1161–1174, 1993.

Ross et al., "Gene therapy in the United States: A five year status report," *Human Gene Therapy*, 7:1781–1790, 1996.

Sharma et al., "Enhance expression of inducible nitric oxide synthase in murine macrophages and glomerular mesangial cells by elevated glucose levels: Possible mediation via protein kinase $C^+$," *Biochem. Biophys. Res. Comm.*, 207(1):80–88, 1995.

Steinberg et al., "Transgenic rat models of inherited retinal degeneration caused by mutant opsin genes," *Inv. Ophth. Vis. Sci.*, 37:S698, Abstract, 1996.

Timmers, Newton an Hauswirth, "Synthesis and stability of retinal photoreceptor mRNAs are coordinately regulated during bovine fetal development," *Exp. Eye Res.*, 56:257–265, 1993.

van Ginkel and Hauswirth, "Parallel regulation of fetal gene expression in different photoreceptor cell types," *The Journal of Biological Chemistry*, 269(7):4986:4992, 1994.

Verma and Somia, "Gene therapy—promises, problems and prospects," *Nature*, 389:239–242, 1997.

von Weizsäcker, Blum and Wands, "Cleavage of hepatitis B virus RNA by three ribozymes transcribed from a single DNA template," *Biochemical and Biophysical Research Communications*, 189(2):743–748, 1992.

Xiao et al., "Efficient long–term gene transfer into muscle tissue of immunocompetent mice by adeno–associated virus vector," *Journal of Virology*, 70(11):8098–8108, 1996.

Xing and Whitton, "An anti–lymphocytic choriomeningitis virus ribozyme expressed in tissue culture cells diminishes viral RNA levels and leads to a reduction in infectious viral yield," *Journal of Virology*, 67(4): 1840–1847, 1993.

Yu et al., "A hairpin ribozyme inhibits expression of diverse strains of human immunodeficiency virus type 1," *Proc. Natl, Acad. Sci. USA*, 90:6340–6344, 1993.

Yu et al., "In vitro an in vivo characterization of a second functional hairpin ribozyme against HIV–1," *Virology*, 206(1):381–386, 1995.

Yung, "Molecular modulation of vascular entothelian growth factor (VEGF) expression in glioma cells by ribozymes," *Neurology*, 48(3 Suppl. 2):A22, Abstract V13.001, 1997.

Zolotukhin et al., "A humanized green fluorescent protein cDNA adapted for high–level expression in mammalian cells," *Journal of Virology*, 70(7):4646–4654, 1996.

Millington–Ward, Sophia, Brian O'Neill, Gearoid Tuohy et al., (1997) "Strategems in vivo for gene therapies directed to dominant mutations," *Human Molecular Genetics*, 6(9):1415–1426.

Drenser, Kimberly A., Adrian M. Timmers, William W. Hauswirth, Alfred S. Lewin (1998) "Ribozyme–targeted destruction of RNA associated with autosomal–dominant retinitis pigmentosa," *Investigative Ophthalmology & Visual Science*, 39(5):681–689.

Drenser, K.D. et al. (1997) "Ribozyme mediated degredation of the P23H and S334Ter mutant mRNAs associated with ADRP," *Investigative Opthalmology& Visual Science*, 38(4):S441, Abstract 2085, 1997 (Annual Mtg. Of the Association for Research in Vision and Opthalmology, Fort Lauderdale, Fl, USA, Jay 11–16, 1997).

Drenser et al. (1996) "Ribozyme Mediated Destruction Of An Messenger–RNA Causing Retinitis Pigmentosis," *Investigative Ophthalmology& Visual Science*, 37(3):S10, Abstract 42.

Altschuler, Mitchell, Richard Tritz, Arnold Hampel (1992) "A method for generating transcripts with defined 5' and 3' termini by autolytic processing," *Gene*, 122:85–90.

Cech, Thomas R. (1990) "Self–splicing of Group I introns," *Annu. Rev. Biochem*, 59:543–568.

Chakravathy, U., Alan W. Stitt, J, McNally, Janice R. Bailie, Elizabeth M. Hoey, Paul Duprex (1995) "Nitric oxide synthase activity and expression in retinal capillary endothelial cells and pericytes," *Curr. Eye Res.*, 14(4):285–294.

Cipolla, Marilyn J., John M. Porter, George Osol (1997) "High Glucose Concentrations Dilate Cerebral Arteries and Diminish Myogenic Tone Through an Endothelial Mechanism," *Stroke*, 28(2):405–411.

Cosentino Francesco, Keiichi Hishikawa, Zvonimir S. Katusic, Thomas F. Lüscher (1997) "High Glucose Increases Nitric Oxide Synthase Expression And Superoxide Anion Generation in Human Aortic Endothelial Cells," *Circulation*, 96(1):25–28.

Daiger, Stephen P., Lori S. Sullivan, Joseph A. Rodriguez (1995) "Correlation of phenotype with genotype in inherited retinal degeneration," *Behavioral and Brain Sciences*, 18:452–467.

DesJardin, Lucy E., William W. Hauswirth (1996) "Developmentally Important DNA Elements Within The Bovine Opsin Upstream Region," *Investigative Ophthalmology & Visual Science*, 37(1):154–165.

Flannery, John G., Sergei Zolotukhin, M. Isabel Vaquero, Matthew M. LaVail, Nicholas Muzyczka, William W. Hauswirth (1997) "Efficient photoreceptor–targeted gene expression in vivo by recombinant adenoassociated virus," *Proc. Natl. Acad. Sci. USA*, 94(13):6916–6921.

Gade, Prasad V., José A. Andrades, Marcel E. Nimni José Becerra, James Longoria, Nadereh Asemanfar, Nino Sorgente (1997) "Nitric oxide mediates hyperglycemia–induced defective migration in cultured endothelial cells," *Journal of Vascular Surgery*, 26(2):319–326.

Goldstein, Ira M., Philipp Ostwald, Steven Roth (1996) "Nitric Oxide: A Review of Its Role in Retinal Function and Disease," *Vision Res.*, 36(18):2979–2994.

Hangai, Masanori, Nagahisa Yoshimura, Kano Hiroi, Michiko Mandai, Yoshihito Honda (1996) "Injury," *Exp. Eye Res.*, 63(5):501–509.

Koizumi, Makoto, Kiroyuki Kamiya, Eiko Ohtsuka (1992) "Ribozymes designed to inhibit transformation of NIH3T3 cells by the activated c–Ha–ras gene," *Gene*, 117:179–184.

Little,Edward and Amy S. Lee (1995) "Generation of a Mammalian Cell Line Deficient in Glucose–Regulated Protein Stress Induction Through Targeted Ribozyme Driven By a Stress–Inducible Promoter," *The Journal of Biological Chemistry*, 270(16):9526–9534.

Ojwang, Joshua O., Arnold Hampel, David J. Looney, Flossie Wong–Staal, Jay Rappaport (1992) "Inhibition of human immunodeficiency virus type 1 expression by a hairpin ribozyme," *Proc. Natl. Acad. Sci. USA*, 89:10802–10806.

Ostwald, Philipp, Ira M. Goldstein, Alex Pachnanda, Steven Roth (1995) "Effect of Nitric Oxide Synthase Inhibition on Blood Flow After Retinal Ischemia in Cats," *Investigative Ophthalmology & Visual Science*, 36(12):2396–2403.

Timmers, Adrian M., Bruce R. Newton, William W. Hauswirth (1993) "Synthesis and Stability of Retinal Photoreceptor mRNAs are Coordinately Regulated During Bovine Fetal Development," *Exp. Eye Res.*, 56:257–265.

van Ginkel, Paul R., William W. Hauswirth (1994) "Parallel Regulation of Fetal Gene Expression in Different Photoreceptor Cell Types," *The Journal of Biological Chemistry*, 269(7):4986:4992.

von Weizsäcker, Fritz, Hubert E. Blum, Jack R. Wands (1992) "Cleavage of hepatitis B virus RNA by three ribozymes transcribed from a single DNA template," *Biochemical and Biophysical Research Communications*, 189(2):743–748.

Xing, Zheng, J. Lindsay Whitton (1993) "An Anti–Lymphocytic Choriomeningitis Virus Ribozyme Expressed in Tissue Culture Cells Diminishes Viral RNA Levels and Leads to a Reduction in Infectious Viral Yield," *Journal of Virology*, 67(4): 1840–1847.

Yu, Mang, Joshua Ojwang, Osamu Yamada, Arnold Hampel, Jay Rapapport, David Looney, Flossie Wong–Staal (1993) "A hairpin ribozyme inhibits expression of diverse strains of human immunodeficiency virus type 1," *Proc. Natl, Acad. Sci. USA*, 90:6340–6344.

Yu, M., E. Poeschia, O. Yamada et al., (1995) "In vitro an In vivo Characterization of a Second Functional Hairpin Ribozyme Against HIV–1," *Virology*, 206(1):381–386.

Zolotukhin, Sergei, Mark Potter, William W. Hauswirth, John Guy, Nicholas Muzyczka (1996) "A Humanized Green Fluorescent Protein cDNA Adapted for High–Level Expression in Mammalian Cells," *Journal of Virology*, 70(7):4646–4654.

Steinberg, R. H., J.G. Flannery, M. I. Naash et al. (1996) Inv. Ophth. Vis. Sci. 37:S698 abstract.

Co–pending U.S. Patent application Ser. No. 09/063,792, filed Apr. 21, 1998 (4300.011400).

* cited by examiner

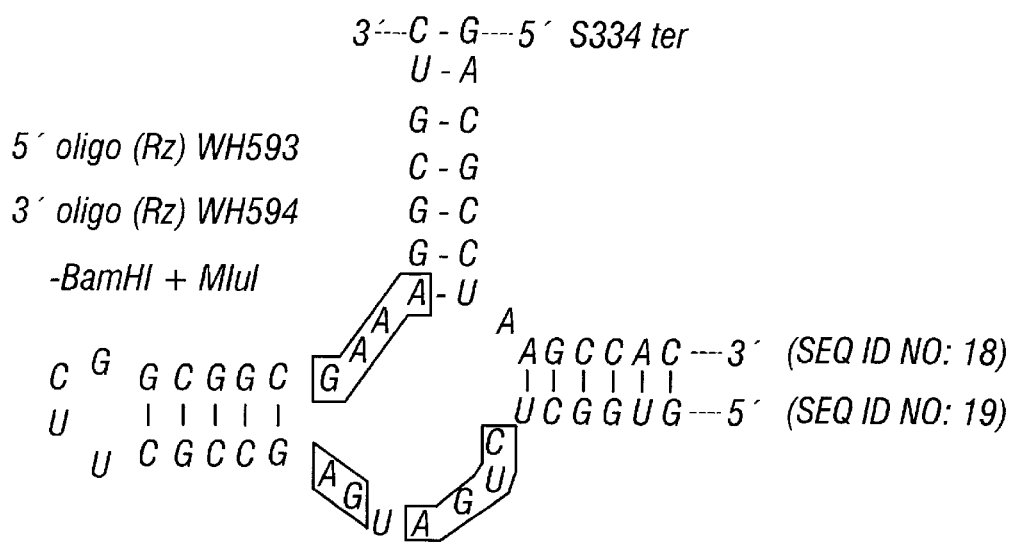
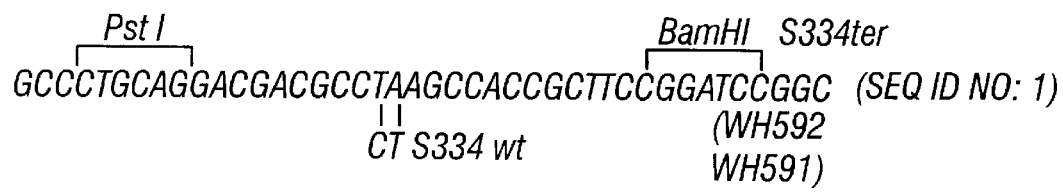
FIG. 3

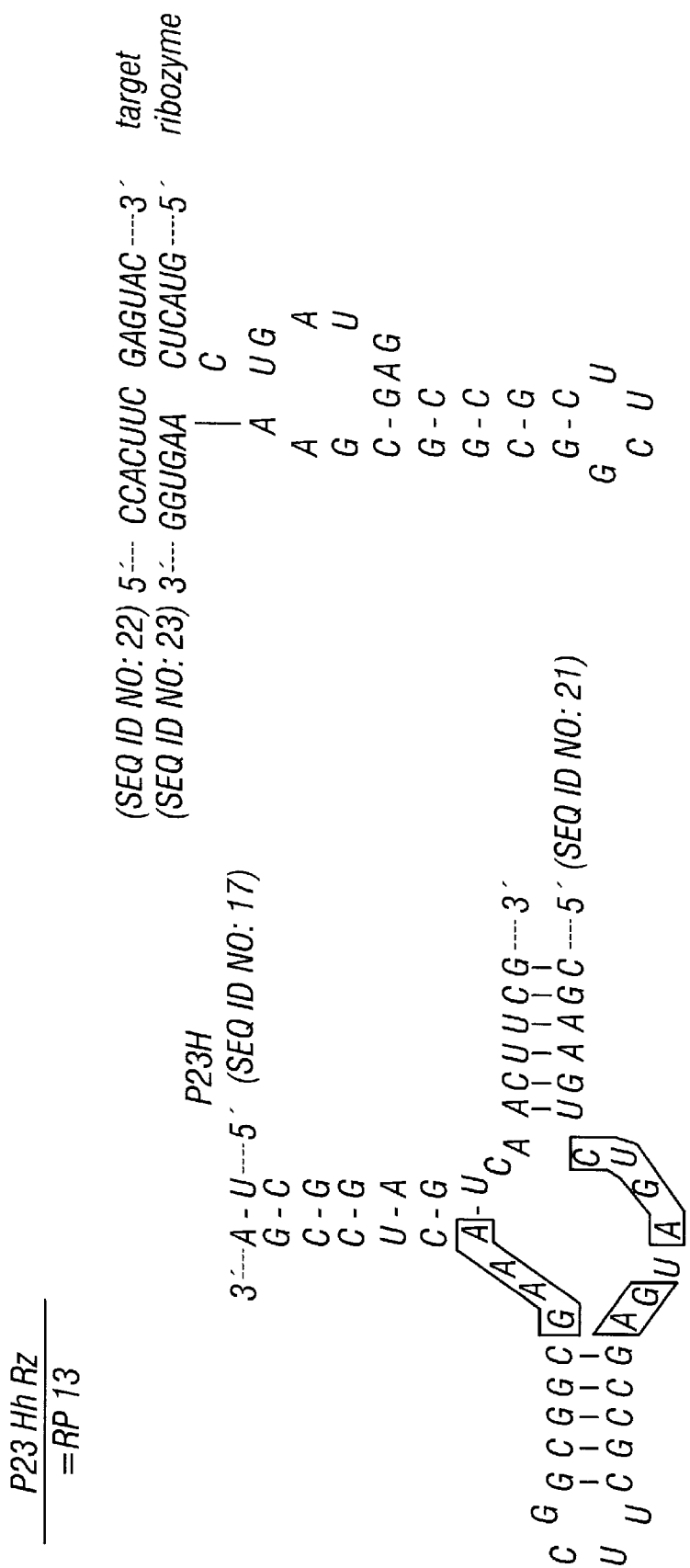

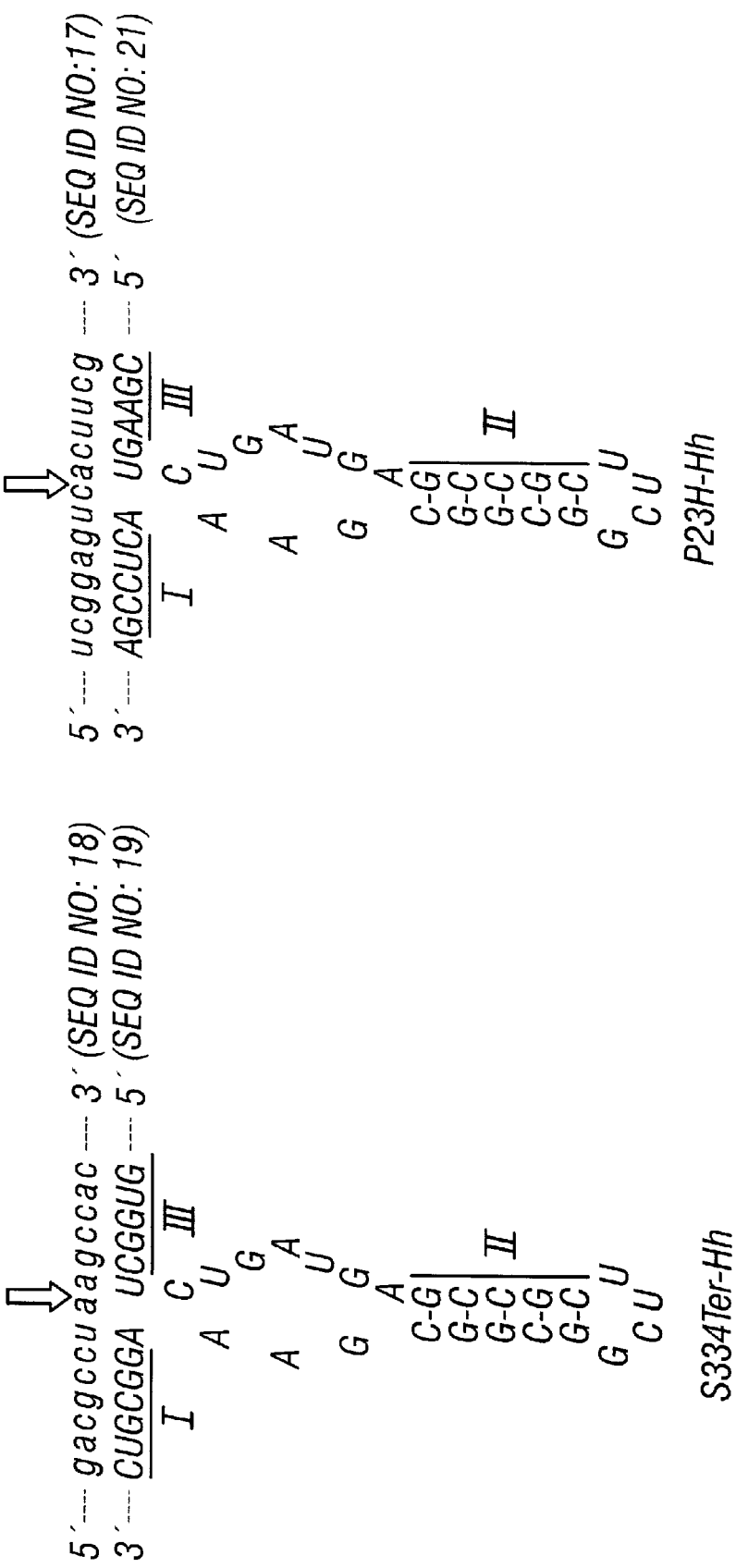

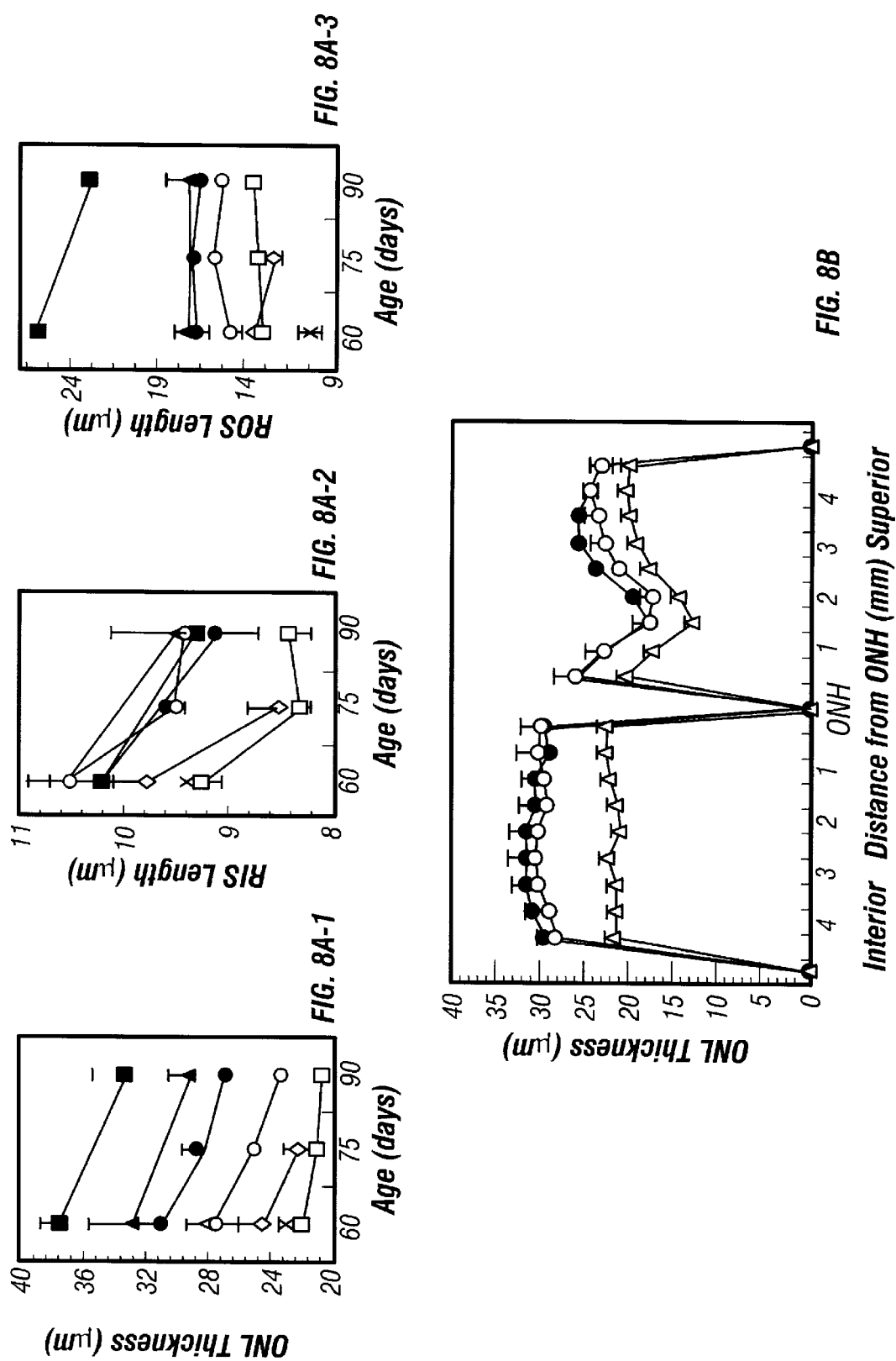

ROD OPSIN MRNA-SPECIFIC RIBOZYME COMPOSITIONS AND METHODS FOR THE TREATMENT OF RETINAL DISEASES

CROSS-REFERENCE TO RELATED APPLICATIONS

This application claims priority from provisional applications U.S. Ser. No. 60/046,147, filed May 9, 1997; and U.S. Ser. No. 60/044,492, filed Apr. 21, 1997.

The subject invention was made with government support under a research project supported by NIH Grant No. EY08571. The government has certain rights in this invention.

BACKGROUND OF THE INVENTION

Ribozymes are biological catalysts consisting of only RNA. They promote a variety of reactions involving RNA and DNA molecules including site-specific cleavage, ligation, polymerization, and phosphoryl exchange (Cech, T. R. [1989] Biochem. Int. 18(1):7–14; Cech, T. R. [1990] Annu. Rev. Biochem. 59:543–569). Ribozymes fall into three broad classes: (1) RNAse P, (2) self-splicing introns, and (3) self-cleaving viral agents. Self-cleaving agents include hepatitis delta virus and components of plant virus satellite RNAs that sever the RNA genome as part of a rolling-circle mode of replication. Because of their small size and great specificity, ribozymes have the greatest potential for biotechnical applications. The ability of ribozymes to cleave other RNA molecules at specific sites in a catalytic manner has brought them into consideration as inhibitors of viral replication or of cell proliferation and gives them potential advantage over antisense RNA. Indeed, ribozymes have already been used to cleave viral targets and oncogene products in living cells (Koizumi, M., H. Kamiya, E. Ohtsuka [1992] Gene 117(2): 179–184; Kashani-Sabet, M., T. Funato, T. Tone et al. [1992] Antisense Res. Dev. 2(1):3–15; Taylor, N. R., J. J. Rossi [1991] Antisense Res. Dev. 1(2): 173–186; von-Weizsacker, F., H. E. Blum, J. R. Wands [1992] Biochem. Biophys. Res. Commun. 189(2):743–748; Ojwang, J. O., A. Hampel, D. J. Looney, F. Wong-Stall, J. Rappaport [1992] Proc. Natl. Acad. Sci. USA 89(22): 10802–10806; Stephenson, P., I. Gibson [1991] Antisense Res. Dev. 1(3):261–268; Yu, M., J. Ojwang, O. Yamada et al. [1993] Proc. Natl. Acad. Sci. USA 90(13):6340–6344; Xing, Z., J. L. Whitton [1993] J. Virol. 67(4):1840–1847; Yu, M., E. Poeschla, O. YamadaetaL [1995] Virology 206(1): 381–386; Little, E., A. S. Lee [1995] J. Biol. Chem. 270 (16):9526–9534).

Two kinds of ribozymes have been employed widely, hairpins and hammerheads. Both catalyze sequence-specific cleavage resulting in products with a 5' hydroxyl and a 2',3'-cyclic phosphate. Hammerhead ribozymes have been used more commonly, because they impose few restrictions on the target site. Hairpin ribozymes are more stable and, consequently, function better than hammerheads at physiologic temperature and magnesium concentrations.

A number of patents have issued describing various ribozymes and methods for designing ribozymes. See, for example, U.S. Pat. Nos. 5,646,031; 5,646,020; 5,639,655; 5,093,246; 4,987,071; 5,116,742; and 5,037,746. However, the ability of ribozymes to provide therapeutic benefit in vivo has not yet been demonstrated.

There are more than 200 inherited diseases that lead to retinal degeneration in humans. Considerable progress has been made in identifying genes and mutations causing many forms of inherited retinal degeneration in humans and other animals. Diseases causing inherited retinal degeneration in humans can be classified broadly into those that first affect peripheral vision and the peripheral retina, such as retinitis pigmentosa, and those that primarily affect central vision and the macula, such as macular dystrophy. The macula has the highest concentration of cones and the peripheral retina is dominated by rods.

Retinitis pigmentosa (RP) is a collection of heritable retinal degenerations caused by defects in one of several genes for proteins of photoreceptor(PR) cells. RP is characterized by progressive rod photoreceptor degeneration and eventual blindness. The exact molecular pathogenesis of RP is still unexplained. Ultrastructural observations suggest that the rod PRs are severely affected in the disease. Approximately 50,000 individuals in the United States are estimated to have RP. The clinical symptoms of retinitis pigmentosa include night blindness and loss of peripheral vision. With time visual impairment progresses toward the center of the retina causing "tunnel-vision."

Retinitis pigmentosa can be subdivided into several genetic categories: antosomal dominant (adRP), autosomal recessive (arRP), X-linked (xIRP) or syndromic. There are also a number of clinical classes for retinitis pigmentosa. These classes have been condensed into two broad categories. Type 1 retinitis pigmentosa is characterized by rapid progression and diffuse, severe pigmentation; type 2 retinitis pigmentosa has a slower progression and more regional, less severe pigmentation.

Macular degeneration is a deterioration of the macula (the cone-rich center of vision) leading to gradual loss of central vision. Eventual loss of these cones leads to central vision loss and functional blindness. At least 500,000 individuals are estimated to suffer from macular degeneration currently in the United States. Macular degeneration can have either a genetic basis or it may be an acquired disease. Approximately 10% of Americans over the age of 50 are afflicted with age-related macular degeneration, an acquired form of disease. The inherited forms of macular degeneration are much less common but usually more severe. Inherited macular degeneration is characterized by early development of macular abnormalities such as yellowish deposits and atrophic or pigmented lesions, followed by progressive loss of central vision.

There is currently no effective treatment for most forms of retinitis pigmentosa or macular degeneration. Treatment with a massive supplement (15,000 I.U. per day) of vitamin A often retards the course of retinal degeneration in retinitis pigmentosa. Vitamin therapy does not treat the underlying cause of RP and is not a cure.

There are many other inherited diseases that cause retinal degeneration in humans. Among these are gyrate atrophy, Norrie disease, choroideremia and various cone-rod dystrophies. In addition there are numerous inherited systemic diseases, such as Bardet-Biedl, Charcot-Marie-Tooth,and Refsum disease which include retinal degeneration among a multiplicity of other symptoms.

Another important ocular disease is diabetic retinopathy. Diabetic retinopathy is the leading cause of blindness in adults between the ages of 18–72. Histological studies consistently implicate endothelial cell dysfunction in the pathology.

Hyperglycemia directly contributes to the development of diabetic retinopathy, and early in the development of diabetic retinopathy there exists disruption of the blood-retinal barrier. NOS activity, as determined by conversion of arginine to citrulline, is significantly increased in diabetes Rosen, P., T. M. Danoff, A. DePiero, F. N. Ziyadeh [1995] *Biochem. Biophys. Res. Commun.* 207(1):80–88). Gade and coworkers demonstrated that endothelial cell dysfunction correlated with elevated glucose in an in vitro wound model and was mediated by increased levels of NO (Gade, P. V., J. A. Andrades, M. E. Nemni et al. [1997] *J. Vasc. Surg.* 26(2):319–326). In rat cerebral arteries acute glucose exposure dilates arteries via an endothelium mediated mechanism that involves NO (Cipolla, M. J., J. M. Porter, G. Osol [1997] *Stroke* 28(2):405–411). Cosentino demonstratedthat prolonged exposure to high glucose increases eNOS gene expression, protein synthesis, and NO release Cosentino, F., K. Hishikawa, Z. S. Katusic, T. F. Luscher [1997] *Circulation* 96(1):25–28).

Nitric oxide (NO) is a pleiotropic molecule with multiple physiological effects: neurotransmitter, component of the immune defense system, regulator of smooth muscle tone and blood pressure, inhibitor of platelet aggregation and a superoxide scavenger. NO is synthesized as a product of the conversion of L-arginine into L-citrulline by the so-called constitutive nitric oxide synthase (NOS), either neuronal (NNOS) or endothelial (eNOS) isoforns. NO regulates specific protein levels. NO increases mRNA levels for VEGF and iNOS.

Although several studies on NO function in the retina have been published, very little information is available pertaining to its role in the diabetic retina (Chakravarthy, U., A. W. Stitt, J. McNally et al. [1995] *Curr. Eye Res.* 14(4): 285–294; Goldstein, I. M., P. Ostwald, S. Roth [1996] *Vision Res.* 36(18):2979–2974). The iNOS isoform is expressed in the retina, as shown by RT-PCR and immunocytochemistry. It is believed to be involved in the development of diabetic retinopathy and in ischemia-reperfusion injury Hangai, M., N. Yoshimura, K. Hirioi, M. Mandai, Y. Honda [1996] *Exp. Eye Res.* 63(5):501–509; Ostwald, P., I. M. Goldstein, A. Pachnanda, S. Roth [1995] *Invest. Ophthalmol. Vis. Sci.* 36(12):2396–2403). Administering NOS inhibitors can ameliorate or prevent ischemia-reperfusioninjury (Lam, T. T., M. O. Tso [1996] *Res. Commun. Mol. Pathol. Pharmacol.* 92(3):329–340). Diabetic human retinal pigmented epithelial cells have augmented iNOS compared to non-diabetic cells. An increasing body of evidence indicates growth factors including vascular endothelial growth factor (VEGF) and insulin-like growth factor-I (IGF-I) are involved in increased permeability of endothelium that leads to breakdown of the blood-retinal barrier in this microvascular disease. However, the mechanisms for growth factor action in disease progression remain elusive.

BRIEF SUMMARY OF THE INVENTION

The subject invention concerns materials and methods for the treatment of diseases involving the expression of abnormal and/or excessive amounts of proteins. More specifically, the subject invention provides polynucleotide sequences, and methods for using these sequences, to achieve highly specific elimination or reduction of messenger RNA encoding abnormal and/or excess proteins in the retina. As described herein, the materials and methods of the subject invention can be used to treat a variety of diseases. In a preferred embodiment, the disease which is treated is a disease of the retina. Specifically exemplified herein are materials and methods which can be used to treat autosomal dominant retinitis pigmentosa (ADRP). Also specifically exemplified are materials and methods for the treatment or prevention of diabetic retinopathy.

In a specific embodiment of the subject invention, hammerhead and hairpin ribozymes have been designed to cleave mutant forms of messenger RNA (mRNA) occurring in various forms of inherited retinal degeneration. The catalytic domain of each ribozyme has been designed to have high stability. In a specific embodiment, the targeting domains are designed to cleave mRNA encoding the P23H mutation. This mutation leads to one of the most common forms of retinitis pigmentosa. These ribozymes have been shown to digest RNA containing the mutation, but not RNA containing the normal sequence. This specificity makes these ribozymes able to destroy harmful mRNA while leaving normal mRNA intact. Ribozymes against other genetic forms of retinitis pigmentosa can be produced and used according to the subject invention.

A further aspect of the subject invention pertains to the reduction and/or elimination of pathological levels of proteins involved in endothelial cell nitric oxide (NO) regulation. This aspect of the subject invention provides materials and methods for the treatment and/or prevention of diabetic retinopathy. Increased inducible nitric oxide synthase (iNOS), enhanced vascular endothelial growth factor levels, and disruption of the blood retinal barrier has been identified in the retinas of BBZ/Wor diabetic rats compared to non-diabetic age-matched controls. Additionally, endothelial NOS (eNOS) has been identified in the plasmalemmal caveolae of retinal capillary endothelium from diabetic animals, and cytological evidence indicates translocation of the caveolae from the lumenal to the ablumenal surface of the endothelium. In high glucose environments, chronically increased NO activity results in endothelial cell dysfunction and impaired blood-retinal barrier integrity responsible for the development of diabetic retinopathy.

A schematicdiagram illustratingkey factorsin the cascading mechanisms responsible for damaged retinal endothelium, blood retinal barrier integrity, and diabetic retinopathy is shown in FIG. 1.

Specific embodiments of this aspect of the subject invention pertain to strategies designed to maintain blood retinal barrier integrity. Three mechanisms for increased NO activity in diabetic endothelial cells can be targeted: (a) growth factors which increase eNOS; (b) cytokines which increase iNOS; (c) glucose which directly increases growth factors, cytokines, and NOS isoforms. Three specific targets for the ribozymes of the subject invention are the messenger RNAs which encode VEGF, iNOS, and eNOS.

The ribozymes of the subject invention can be delivered using any one of a variety of methods. In a preferred embodiment, recombinant Adeno-associated Virus (rAAV) vectors can be used to transfer the desired genes to retina cells with efficient and cell type-specific expressionofthe exogenousgenes in photoreceptorcells. Other methods of delivery including the use of other viral vectors, liposomes, and naked DNA delivery can be utilized. With the benefit of the teachings provided herein, a person skilled in the art can readily identify, prepare, and use vectors which deliver the ribozymes of the subject invention to the desired location.

A major advantage of using AAV relative to retrovirus-based vectors include its lack of pathogenicity, its ability to infect a broad variety of cells and tissues, and its ability to infect growth-arrested cells. Recombinant AAV lacking its normal rep and cap genes are currently used for gene delivery. The small size of AAV (20 nm in diameter) makes it more permeable to retinal tissues than adenovirus. High titers of AAV are attainable in tissue culture, and the stable virion can be concentrated to reasonably high titers (up to 1012 infectious virus per ml). Even though up to 90% of the human population has been exposed to AAV, there is no association with human disease, making AAV inherently safer than herpesvirus or adenovirus based vectors.

BRIEF SUMMARY OF THE DRAWINGS

FIG. 3 shows the structure of a ribozyme (S334Ter hammerhead ribozyme Rp9; SEQ ID NO:19) useful according to the subject invention, along with the S334Ter mutant target sequence (SEQ ID NO:18) and the constructed oligonucleotide sequence (SEQ ID NO:1).

FIG. 5 shows the structure of a ribozyme (P23H hammerhead ribozyme Rp13; SEQ ID NO:21) useful according to the subject invention, along with the P23H mutant target sequence (SEQ ID NO:17).

FIG. 6 shows the structure of a ribozyme (P23H hammerhead ribozyme Rz23; SEQ ID NO:23) useful according to the subject invention.

FIGS. 7A and 7B show the secondary structure of the P23H (SEQ ID NO:21) and S334Ter (SEQ ID NO:19) hammerhead ribozymes (FIG. 7A) and the P23H (SEQ ID NO:20) hairpin ribozyme (FIG. 7B). The uppercase letters represent the ribozyme sequences, and the lowercase letters represent the target RNA sequences. Substrate sequences differing from the wild-type opsin are in bold type. Roman numerals label the helices. Helix IV of the hairpin has been extended by 4 base pairs and loop C converted to a GNRA tetraloop. Arrows indicate the site of cleavage.

FIGS. 8a–8b show outer retinal layer with P23H ribozymes. 8a, measurements of ONL thickness (left), RIS length (middle), and ROS length (right) in rats killed at different ages. Filled squares denote normal, non-transgenic animals. P23H-3 rats were either uninjected (open squares), injected subretinally with PBS (open diamonds), or injected with AAV vectors carrying one of five ribozymes or controls. Ribozymes were: Hp11 hairpin ribozyme (filled circles), Hh13 hammerhead ribozyme (filled triangles), Hp11i "inactive" hairpin ribozyme (open circles), Hh13i "inactive" hammerhead ribozyme (open triangle), or BOPS-gfp (X), all regulated by the same bovine opsin promoter. All injections were performed at P14–15. The error bars were omitted if they fell within the symbol, except for Hp11i at P75 and P90, where only one eye at each point was examined. FIG. 8b, Measurements of ONL thickness along the vertical meridian of the eye from the optic nerve head (ONH) to the ora serrata (anterior margin of the retina) in rats at P90. Rats were either uninjected (open triangles) or injected at P14–15 with Hp11 hairpin ribozymes (filled circles) or Hh13 hammerhead ribozymes (open circles).

BRIEF DESCRIPTION OF THE SEQUENCES

Figure 1:
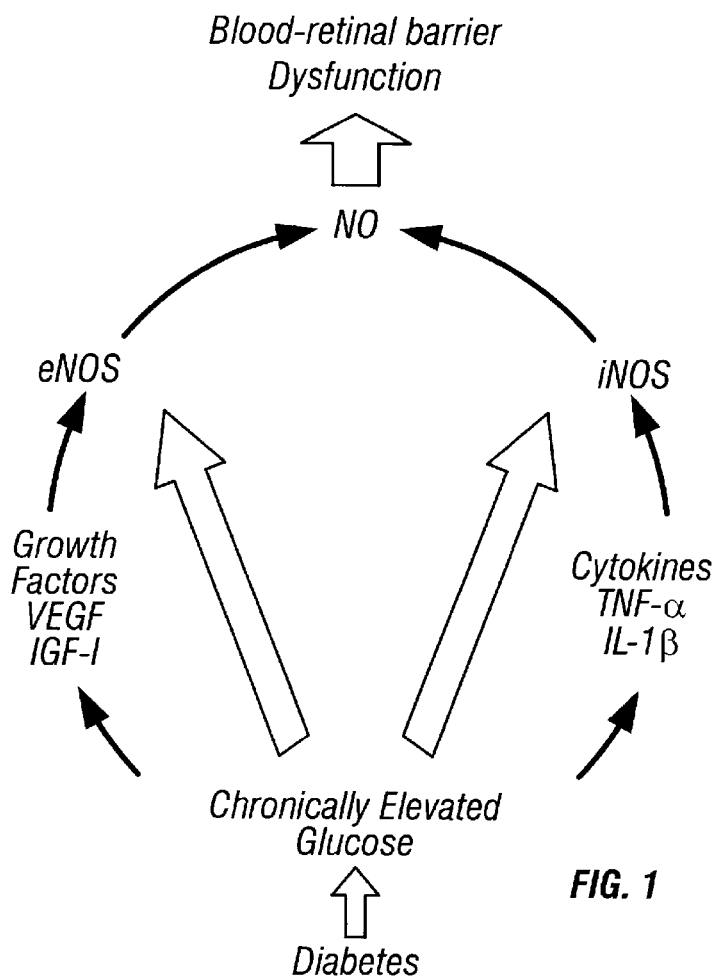
FIG. 1 shows a schematic diagram illustrating key factors in the cascading mechanisms responsible for damaged retinal endothelium, blood retinal barrier integrity, and diabetic retinopathy.

SEQ ID NO. 1 is the constructed oligonucleotide sequence designated S334Ter.

SEQ ID NO. 2 is the constructed oligonucleotide sequence designated P23H.

SEQ ID NO. 3 is the wild-type oligonucleotide sequence S334.

SEQ ID NO. 4 is the wild-type oligonucleotide sequence P23H.

SEQ ID NO. 5 is an overlapping oligonucleotide for the S334Ter hammerhead ribozyme.

SEQ ID NO. 6 is an overlapping oligonucleotide for the S334Ter hammerhead ribozyme.

SEQ ID NO. 7 is an overlapping oligonucleotide for the P23H hammerhead ribozyme.

SEQ ID NO. 8 is an overlapping oligonucleotides for the P23H hammerhead ribozyme.

SEQ ID NO. 9 is an overlapping oligonucleotides for the P23H hairpin ribozyme.

SEQ ID NO. 10 is an overlapping oligonucleotides for the P23H hairpin ribozyme.

SEQ ID NO. 11 is a downstream P23H primer for both mutant and wild-type genes used according to the subject invention.

SEQ ID NO. 12 is an upstream P23H primer for both mutant and wild-type genes used according to the subject invention.

SEQ ID NO. 13 is an upstream P23 primer for wild-type genes used according to the subject invention.

SEQ ID NO. 14 is a downstream S334Ter primer for both mutant and wild-type genes used according to the subject invention.

SEQ ID NO. 15 is an upstream S334Ter primer for both mutant and wild-type genes used according to the subject invention.

SEQ ID NO. 16 is an upstream S334 primer for wild-type genes used according to the subject invention.

SEQ ID NO. 17 is a mutant target sequence used according to the subject invention.

SEQ ID NO:18 is a mutant target sequence (S334Ter) used according to the subject invention.

SEQ ID NO:19 is a ribozyme (S334Ter hammerhead ribozyme Rp9) used according to the subject invention.

SEQ ID NO:20 is a ribozyme (P23H hairpin ribozyme Rp11) used according to the subject invention.

SEQ ID NO:21 is a ribozyme (P23H hammerhead ribozyme Rp13) used according to the subject invention.

SEQ ID NO:22 is a mutant target sequence (P23H) used according to the subject invention.

SEQ ID NO:23 is a ribozyme (P23H hammerhead ribozyme Rz23) used according to the subject invention.

DETAILED DISCLOSURE OF THE INVENTION

The subject invention pertains to methods for achieving highly specific elimination and/or reduction of mutant and/ or excess proteins associated with pathological conditions. Specifically exemplified herein is the use of ribozymes to treat and/or prevent diseases in the retina. In one aspect, the subject invention provides materials and methods which can be used to reduce or eliminate the symptoms of inherited eye disease caused by mutations in genes for retinal proteins.

In a specific embodiment, the subject invention provides a method for treating autosomal dominant retinitis pigmentosa (ADRP) at a molecular level. Twelve percent of American patients with autosomal dominant retinitis pigmentosa carry a substitution of histidine for proline at codon 23 (P23H) in their rhodopsin gene, resulting in photoreceptor cell death from the synthesis of the abnormal gene product. One aspect of the current invention pertains to the use of ribozymes to discriminate and catalyze the destruction of P23H mutant mRNAs. Expression of either a hammerhead or hairpin ribozyme in a rat model markedly slows the rate of photoreceptor degeneration for at least 15 months. Catalytically inactive control ribozymes had significantly lesser effect on retarding the retinal degeneration. Intracellular production of ribozymes in photoreceptors can be achieved, for example, by transduction with a recombinant Adeno-Associated Virus (rAAV) incorporating a rhodopsin promoter.

The subject invention utilizes the catalytic properties of ribozymes. Ribozymes are enzymes comprised of ribonucleic acid (RNA). In nature, ribozymes conduct a variety of reactions involving RNA, including cleavage and ligation of polynucleotide strands. The specificity of ribozymes is determined by base pairing (hydrogen bonding) between the targeting domain of the ribozyme and the substrate RNA. This specificity can be modified by altering the nucleotide sequence of the targeting domain. The catalytic domain of ribozymes, the part that actually performs the biochemical work, can also be changed in order to increase activity or stability of the ribozyme.

Ribozymes, if delivered as described herein to photoreceptor cells of the retina by a gene delivery vector such as a specially designed virus, provide a long-term, even permanent treatment for retinitis pigmentosa, macular degeneration, or other pathological retina condition. Viral vectors, such as rAAV, are well known and readily available to those skilled in the art. Utilizing the techniques of the subject invention, ribozymes can be continuously produced in the retinal cells from a copy of the ribozyme integrated in the patient's DNA.

Figure 4:
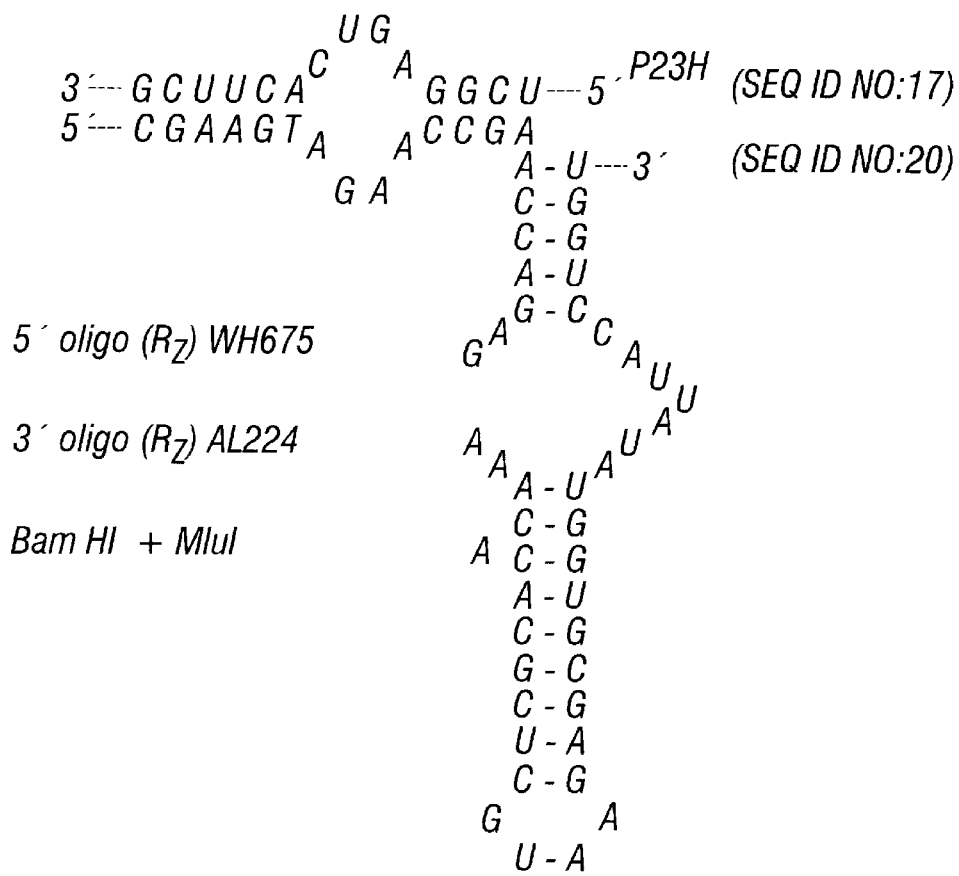
FIG. 4 shows the structure of a ribozyme (P23H hairpin ribozyme Rp11; SEQ ID NO:20) useful according to the subject invention, along with the P23H mutant target sequence (SEQ ID NO:17) and the constructed oligonucleotide sequence (SEQ ID NO:2).

In one embodiment the subject invention concerns synthetic genes for several ribozymes. These ribozymes recognize the nucleotide change causing the P23H mutation in one form of ADRP and the S334ter mutation in another. Genes have been constructed which encode several ribozymes having the ability to specifically destroy target RNAs for mutant retina proteins. Specifically, FIG. 3 shows a ribozyme for the destruction of RNA having the S334 mutation. FIGS. 4, 5, and 6 show ribozymes which destroy RNA having the P23H mutation. The ribozyme in FIG. 6 is a hammerhead ribozyme (Rz23) which is directed against the human P23H mRNA. With the benefit of the teachings provided herein, the skilled artisan can construct genes encoding ribozymes which destroy mutant RNA molecules associated with human RP or other retinal diseases.

Using a recombinant Adeno-associated virus (rAAV) in which expression is driven by a portion of the rod opsin promoter, photoreceptor-specific expression of reporter genes can be achieved by ocular injection. Transgenic rat lines carrying the P23H or S334ter mutation in the rod opsin gene under control of the opsin promoter exhibit a course of retinal disease remarkably similar to that observed in humans bearing such mutations. rAAV-ribozymes in P23H and S334ter can be tested in transgenic rats to confirm that the course of the RP-like disease can be ameliorated with a minimum of pathogenic side effects. Assays for activity include morphological analysis of retinal degeneration, quantitative mRNA studies, and electroretinography.

Ribozymes can also be used according to the subject invention as a partial treatment for recessive or semi-dominant genetic diseases of the eye as a supplement to gene replacement therapy. The delivery-expression materials and methods of the subject invention can be used to replace any gene responsible for recessive photoreceptor disease. Specific examples include the genes responsible for retinitis pigmentosa or macular degeneration. Additionally, ribozymes can be used according to the subject invention to treat RP-like disease resulting from the numerous known mutations in the rhodopsin gene. Examples of such mutations are well known to those skilled in the art. See, for example, Daiger, S. P., L. S. Sullivan, J. A. Rodriguez (1995) *Behavioral Brain Sci.* 18:452–467.

A further aspect of the current invention pertains to therapeutic strategies that can retard or block the effects of high glucose on progression of diabetic retinopathy. High glucose environments can result in chronically increased nitric oxide (NO) activity which leads to endothelial cell dysfunction and impaired blood retinal barrier integrity characteristic of diabetic retinopathy.

Reducing the synthesis of NOS using ribozymes can be used to retard or eliminate the damage to the blood retinal barrier. For example, ribozymes which reduce mRNA for VEGF, iNOS, or eNOS can be used. In specific embodiments, to inhibit the expression of iNOS and eNOS, hammerhead ribozymes that contain one long (46 nt) targeting arm 3' to the catalytic domain and a short (5 nt) targeting sequence 5' to the catalytic domain can be used. The long targeting arm permits rapid association with the target sequence. Keeping one arm short permits rapid dissociation of product necessary for catalytic turnover. Messenger RNA molecules have a complex pattern of intramolecular hydrogen bonds that reduce the portion of the molecule available for ribozyme attack. Sites in the iNOS and eNOS mRNAs accessible to ribozyme binding can be determined using synthetic transcripts of iNOS and eNOS cDNA clones. Ribozyme cleavage can be tested on short oligonucleotides identical to sequences of accessible regions containing hammerhead target sites. The most active ribozymes can then be tested on synthetic transcripts of the entire cDNA clone and on total mRNA extracted from endothelial cells to identify the most preferred ribozymes.

Genes encoding ribozymes can be cloned in the AAV vector or other suitable vector. High-potency ribozymes that cleave eNOS, iNOS, and/or VEGF mRNA can be constructed by those skilled in the art having the benefit of the instant disclosure. Delivering these to retinal endothelial cells can be done to reduce expression of iNOS, eNOS, or VEGF and, ultimately, to reduce the production of nitric oxide. Reduction of NO production will, in turn, reduce or delay retinal permeability dysfunction.

Materials and Methods rAAV Plasmid Construction.

The mOp-lacZ-rAAV plasmid DNA was made by first inserting the 4.3 kbp BglII/BamHI fragment containing the proximal murine rod opsin promoter (+86 to −385) and the entire lacZ gene of clone pRG3 (Lem, J., M. Applebury, J.

Figure 2A:
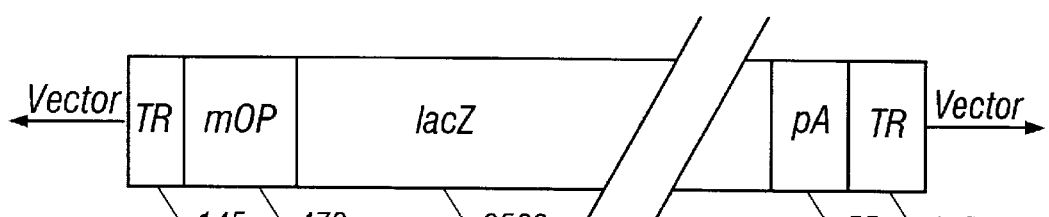
FIGS. 2a and 2b show the construction of plasmids used according to the subject invention. These figures show a schematic diagram of the plasmid DNA constructs used to make rAAV viruses mOp-lacZ (a) and mOp-gfp (b). TR, 145 bp AAV terminal repeat sequence, mOp, 472 bp murine rod opsin regulatory sequence from +86 to −388, SD/SA, 180 bp SV40 late viral protein gene 16S/19S splice donor and acceptor signal, lacZ; coding sequence for the bacterial lacZ gene; gfp, coding sequence for the synthetic green fluorescence gene; pA, pA1 and pA2, polyadenylation signals; Epo, a tandem repeat of the polyoma virus enhancer region (bases 5210–5274); Ptk, thymidine kinase promoter of herpesvirus (bases 92–218); neor, coding sequence of the neomycin resistance gene, Tn5 (bases 1555–2347) (Zolotukhin, S., M. Potter, W. Hauswirth, J. Guy, N. Muzyczka [1996] *J. Virol.* 70:4646–4654).
Figure 2B:
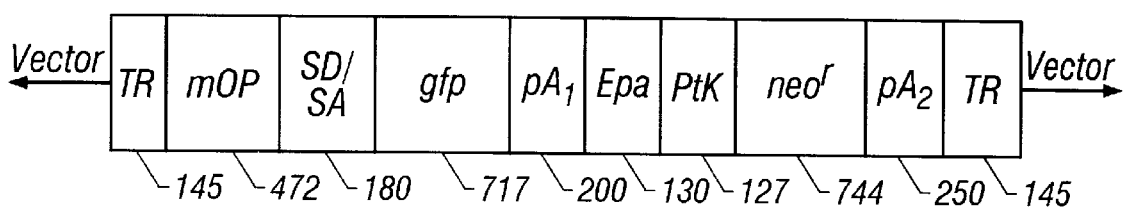

Falk, J. Flannery, M. Simon [1991] *J. Biol. Chem.* 266:9667–9672) into the BglII sites of pTR which contains the AAV TR sequences and a SV40 polyadenylation sequence (FIG. 2a). The mOp-gfp-rAAV plasmid DNA was made by first adding NotI linkers to the 472 bp BglII/XhoI proximal opsin promoter fragment of pRG3 and inserting it into the NotI sites of pTRUF2 (Zolotukhin, S. M. Potter, W. Hauswirth, J. Guy, N. Muzyczka [1996] *J. Virol.* 70:4646–4654) (FIG. 2b).

rAAV Virus Production and Analysis.

To generate recombinant virus, human 293 cells were co-transfected with mOp-lacZ-rAAV or mOp-gfp-rAAV plasmid DNA and the helper pIM45 plasmid DNA carrying the wtAAV genome without terminal repeats (Zolotukhin, S. M. Potter, W. Hauswirth, J. Guy, N. Muzyczka [1996] *J. Virol.* 70:4646–4654). Cultures were then infected with helper Adenovirus, Ad-ts 149 for the lacZ virus or with Ad5 for the gfp virus, at a multiplicity of infection of 10 rAAV and wtAAV titers were determined by infectious center assay (McLaughlin, S. P. Collis, P. Hermonat, N. Muzyczka [1988] *J. Virol.* 62:1963–1973), which is independent of the transgene or opsin promoter used. Titers of contaminating adenovirus were determined by plaque assay for mOp-gfp-rAAV and by serial dilution cytopathic effect for mOp-lacZ-rAAV. Adenovirus was not detectible in either of the rAAV preparations.

Subretinal Injection of rAAV.

Thirty adult C57BL/6I (Jackson Laboratories, Bar Harbor, Me.) pigmented mice between 3 and 6 months of age and 27 adult albino Sprague-Dawley rats between 3 and 4 months of age were used. Animals were anesthetized by ketamine/xylazineinjection, eyes were dilated (2.5% phenylephrine and 0.5% tropicamide) and a local anesthetic (proparacain HCl) was applied. Injections (1 $\mu$l in mice and 2 $\mu$l in rats) were made into the right eye with blunt 32 gauge needle through an opening in the pars-plana, delivering the rAAV suspension into the superior subretinal space. Control injections were made in the contralateral eye with PBS only. Injections were performed with an operating microscope and the subretinal location of the injected volume was confirmed by ophthalmoscopy.

Tissue Analysis.

Animals were euthanized by intramuscular injection of ketamine, followed by phenobarbital overdose. The eyes were immediately enucleated and the site of virus injection marked. The cornea, lens and vitreous of each eye were removed and the posterior eyecup placed in primary fixative.

For β-galactosidase staining, eyecups were fixed in 0.5% glutaraldehyde in 0.1M Cacodylate buffer pH 7.5 for 15 minutes at room temperature. Following a 10 minute wash in PBS, the eyecups were incubated in an iron-based X-gel staining solution (Sanes, J., J. Rubenstein, J. Nicolas [1986] *EMBO J.* 5:3133–3142) in a shaking water bath at 35° C. for 12 hours. For agarose embedment, retinas were detached from the RPE, submerged without dehydration in molten 5% agarose and cooled to 25° C. Retinas were sectioned in the transverse axis in isotonic PBS on a vibratome at 50–100 $\mu$m. Bright field and phase-contrast micrographs of whole mounts and β-galactosidase-stained sections were made with a Zeiss Axiophot.

GFP fluorescence was examined in retinal whole mounts and agarose embedded sections. Tissue fixation was minimized to reduce retinal autofluorescence. Retinas were detached from eyecups, fixed for 15 minutes at room temperature in 4% formaldehyde, 0.1 M $PO_4$ buffer pH 7.5, and rinsed three times in PBS. Whole mounts were photographed with epifluorescence using Zeiss filter set 09 (ex. 450–490 nm, barrier 510 nm, emission 520 nm) and an AttoArc (Carl Zeiss, Inc., New York) variable output UV lamp to minimize GFP bleaching. Whole mount retinas were then embedded in agarose as above for 100 $\mu$m transverse vibratome sections, and fluorescence was documented as for the whole mount. Higher resolution images were collected with a Molecular Dynamics confocal microscope (Nikon 40× or 60×1.4 n.a. oil objectives; argon laser excitation at 514 nm, emission at 520–560 nm). Optical sections were made in 0.32 $\mu$m steps. Full frame (768×512) 8-bit images were collected and processed with Adobe Photoshop. Area measurements were made with NIH Image analysis software (Rasband, W. D. Bright [1995] *Microbeam Analysis Society Journal* 4:137–149).

Expression of the lacZ reporter gene in murine retinal cells was analyzed by reverse transcriptase PCR (RT-PCR). Pieces of retina (1 $mm^2$), were detached from unfixed eyecups and dissected free of RPE, homogenized with a pestle fitted to a 1.5 ml tube and total RNA isolated using the trizol reagent (phenol-guanidineisothiocyanate,Gibco-BRL, Gaithersberg, Md.) according to the manufacturer's recommendations. The RNA was additionally purified over an RNA-easy spin column (Qiagen, Chatsworth, Calif.). The RT-PCR employed a two buffer thermostable Tth polymerase system (Promega, Madison, Wis.) according to manufacturer's instructions and lacZ sequence primers from nucleotides 105 to 124 (forward) and 303 to 286 (reverse). RNAse and DNAse digestions prior to the RT-PCR were performed as previously described (van Ginkel, P., W. Hauswirth [1994] *J. Biol. Chem.* 269:4986–4992).

Following are examples which illustrate procedures for practicing the invention. These examples should not be construed as limiting. All percentages are by weight and all solvent mixture proportions are by volume unless otherwise noted.

EXAMPLE 1

Design of rAAV Vectors for Gene Transfer to Photoreceptors

To express a foreign gene such as a gene encoding a ribozyme specifically in photoreceptor (PR) cells, it is possible to utilize a specifically adapted viral vector. To demonstrate this capability 472 bp of the proximal murine rod opsin promoter (+86 to −385) were linked to a lacZ-SV40 polyA reporter gene and then inserted this into pTR. The gene construct was packaged into AAV virus particles, concentrated, tested for contaminating Adenovirus and titered for recombinant AAV by an infectious center assay. The right eyes of 30 C57B1/6J mice were injected sub-retinally with 1 $\mu$l of mOp-lacZ virus ($10^7$ iu per ml). After two weeks, the right (test) and left (control) eyes of 12 animals were removed, fixed and stained with X-gal. Test retina in 6 of 12 injected eyes exhibited a focal blue region consistent with a subretinal bleb of the injected virus creating a localized retinal detachment. All control eyes showed no X-gal reaction. Reporter gene expression was examined in mice sacrificed at later periods and was detected at 10 weeks post-injection suggesting persistent reporter transgene expression.

EXAMPLE 2

Lac-Z and GFP Reporter Genes are Expressed Exclusively in Photoreceptors

The distribution of lacZ gene product was analyzed at higher resolution by preparing serial 50 $\mu$m transverse sections from the entire whole mounts. The blue X-gal reaction product is observed primarily in the PR inner segments. Most of the PRs were filled with X-gal in this region. X-gal staining was slightly above control levels in the PR synaptic termini in the outer plexiform layer. PR outer segments, RPE and other retinal cells in this region did not reveal X-gal staining above baseline levels observed in identically treated, uninjected or PBS-injected control retinas from the contralateral eye. Examination of additional transverse sections confirmed that the region of positive staining radiated outward from the injection site in a progressively reducing fraction of PR inner segments until baseline levels were seen. The area of X-gal positive PRs was consistent with the blue area in the whole-mount view. Neural retina and RPE were separated and analyzed independently to control for the possibility that the β-galactosidase enzyme or its X-gal reaction product was transferred from transduced RPE cells to PRs. Total mRNA was extracted from neural retina, and RPE from injected animals and tested for the presence of lacZ mRNA by RT-PCR. The 199-bp amplification product diagnostic for lacZ RNA (nucleotides 105 to 303) can be seen when total RNA from a portion of a mouse retina sacrificed at 2 weeks post-injection is amplified. The amplification template was a cellular RNA because of its resistance to DNAse pretreatment and sensitivity to RNAse pretreatment. The remaining RPE tissue was negative for this RT-PCR product. This demonstrates that the observed X-gal product was derived from β-galactosidase expression within PR cells and not derived from RPE expression.

A second reporter gene, a synthetic version of the A victoria green fluorescent gene (gfp) (Zolotukhin, S. M. Potter, W. Hauswirth, J. Guy, N. Muzyczka [1996] *J. Virol.* 70:4646–4654) was used to independently confirm the apparent cell-type specificity of transduction. The same murine rod opsin promoter was used as well as an analogous rAAV vector to construct the mOp-gfp virus (FIG. 2b). Two μl of gfp-containing rAAV was injected into the subretinal space of 8 Sprague-Dawley rats. Rats were used in place of mice because the larger eye allowed more reproducible subretinal inoculations. Retinal whole mounts prepared from all eight rat eyes that were injected contained a fluorescent region of superior retina surrounding the site of inoculation. GFP fluorescence typically extended over 10–20% of the retinal area in a radial pattern from the injection site. Immediately surrounding the point of infection, the transduction frequency, as judged by the intensity of GFP fluorescence, was very high, with a continuous positive signal. In transverse sections extending from the central retina to the periphery, beyond a region of apparently saturated GFP fluorescence, the percentage of transduced cells decreased radially with distance from the injection site. GFP-positive cells were easily identifiable as PRs by their specialized shape and location in the retina. Hence, only PR cells appeared to have been transduced, i.e., infected by the rAAV and expressing the gfp passenger gene.

EXAMPLE 3
Opsin Promoter Confers Photoreceptor Cell Specificity

The PR-specific pattern of GFP expression was confirmed by laser confocal microscopy. GFP was not observed between the inner limiting membrane (vitreal face of the inner retina) and the outer plexiform layer (OPL) (junction of the inner retina with PR synaptic termini). This region contains all the non-PR retinal neuronal (bipolar, horizontal, amacrine, and ganglion) and glial (Müller) cells. Virtually 100% of the PR inner segments, cell bodies, and synaptic terminals exhibited strong GFP fluorescence. In regions more peripheral to the injection site, the fraction of positive PRs was substantially reduced, consistent with the radial decline in fluorescence seen in retinal whole mounts. We established that all PR cell bodies contained GFP signal by examining serial optical sections (0.32 μm). Through-focus series demonstrated that occasional, dark regions in the ONL always contained a gfp-positive PR cell body in another plane of section. Therefore, all PRs, including both rods and cones, supported reporter gene expression. Outer segments demonstrated less fluorescence than other PR compartments, near the level of autofluorescence seen in control outer segments. No GFP signal was observed in the REP, choroid, or sciera.

EXAMPLE 4
Construction of Plasmids Encoding the Substrate RNA and Ribozymes

Two duplex synthetic DNA oligonucleotides containing the target coding sequences and flanked by PstI and BamHI restriction sites were ligated into the plasmid pT7/T3–19 (Life Technologies, Gaithersburg, Md.) downstream of a T7 RNA polymerase promoter. The sequences of the target oligonucleotides were S334Ter: 5'-GCCCTGCAGG ACGACGCCTA AGCCACCGCTTCCGGATCCGGC-3' (SEQ ID NO. 1); and P23H: 5'-GCCCTGCAGG GTCG-GAGTCA CTTCGAGCAG GGATCCGGC-3' (SEQ ID NO. 2). The wild-type target oligonucleotide sequences were S334: 5'-GCCCTGCAGG ACGACGCCTC TGCCACCGCTTCCGGATCCGGC-3' (SEQ ID NO. 3); and P23H: 5'-GCCCTGCAGG GTCGGAGCCC CTTC-GAGCAG GGATCCGGC-3' (SEQ ID NO. 4).

Ribozyme were generated by extension of two overlapping synthetic DNA oligonucleotides flanked by KpnI and MluI restriction sites. The large fragment of DNA pol I (Klenow; NEB, Beverly, Mass.) was used as follows to fill out the DNA duplexes: Overlapping oligonucleotides were heated to 65° C. for 2 minutes and annealed by slow cooling to room temperature for 30 minutes. The annealed oligonucleotides primed each other and were mutually extended by DNA polymerase in the presence of 5 mM deoxynucleoside triphosphates and polymerase buffer (10 mM Tris-HCl [pH 7.5], 5 mM $MgCl_2$, and 7.5 mM dithiothreitol) for 1 hour at 37° C. The fully duplex fragments were digested and ligated into the T7 RNA polymerase expression plasmid pHC[40] at the KpnI and MluI restriction sites. Ligated plasmids were transformed into *Escherichia coli* DH5-α cells. Clones were screened by hybridization analysis and were verified by sequencing.

In the S334Ter hammerhead, sequences of the overlapping oligonucleotides for each ribozyme were: 5'-GCGCGGTACCGTGGCTCTG <u>A</u>TGA<u>G</u>CC GCTT-CGGC-3' (SEQ ID NO. 5) and 5'-GCGCACGCG-TGACGCCTTTC <u>G</u>CCGCCGAAGCGGC-3' (SEQ ID NO. 6); in the P23H hammerhead: 5'-GCGCGGTACC CGAAGTCTG <u>A</u>TGA<u>G</u>CCGCT TCGGC-3' (SEQ ID NO. 7) and 5'-GCGCACGCGT TCGGAGTTTC <u>G</u>CCGCCGAAG CGGC-3' (SEQ ID NO. 8); and in the P23H hairpin: 5'-GCGCGGTACC GAAGTAGAAC CGAACCAGAG AAACA-3' (SEQ ID NO. 9) and 5'-GCGCACGCGT ACCAGG<u>T</u>AAT ATAC<u>C</u>ACGCT CTTACGAGCG TGTGTTTCTC TGGTT-3' (SEQ ID NO. 10). Underlined nucleotides were mutated in a second set of oligonucleotides(hammerhead: A-C, G-C, G-T; hairpin: T-A, C-G) to create inactive ribozymes as controls.

In Vitro Transcription.

Plasmids containing target sequences were linearized with BamHI, and plasmids containing ribozyme sequences with MluI. All transcripts were generated with T7 RNA polymerase and were labeled by incorporation of [α-$^{32}$P] uridine triphosphate (ICN; Costa Mesa, Calif.). Transcriptionreactions were brought to 0.5% sodium dodecyl sulfate, extracted with phenol-chloroform-isoamyl alcohol (50:50:1), precipitated with ethanol, washed twice with 70% ethanol, and resuspended in water. For hairpin ribozymes, ethanol precipitation was replaced by gel filtration Sephadex G-50 (Pharmacia; Uppsala, Sweden) columns.

RNA Extraction.

Total RNA was extracted from the retinas of the P23H and S334Ter transgenic rats (RNeasy Mini-preps; Qiagen, Santa Clara, Calif.) according to the manufacturer's recommendations. Retinas were snap frozen in liquid nitrogen before RNA extraction and stored at −70° C. A typical preparation resulted in 100 μg total RNA.

Ribozyme Cleavage Reactions.

Specific radioactivity of the [α-$^{32}$P] uridine triphosphate and the base composition of each molecule were used to calculate the concentration of target and ribozyme molecules. Standard cleavage conditions consisted of 50 nM substrate RNA and 20 nM ribozyme, 20 mM MgCl$_2$, 40 mM Tris-HCl (pH 7.5), and incubation at 37° C. Hammerhead ribozymes were renatured by incubation in 10 mM MgCl$_2$ at 37° C. for 4 to 10 hours. Hairpin ribozymes were denatured at 90° C. for 2 minutes in 0.1 mM EDTA and renatured at room temperature for 5 minutes. Cleavage reactions were started with the addition of MgCl$_2$. Reactions were stopped by addition of 50 mM EDTA, than an equal volume of 10 M urea, 0.002% bromphenol blue, and 0.002% xylene cyanol. Experimental conditions, such as time of incubation, magnesium concentration, and ribozyme concentration, were varied individually. All reactions were performed in a final volume of 15 μl. Cleavage assays with the retinal RNAs as target substrates contained 0.1 μg total RNA extract and 50 nM ribozyme. Cleavage products were analyzed by electrophoresis on 8 M urea 10% acrylamide sequencing gels (run in 0.089 M Tris-borate, 0.089 M boric acid, and 0.002 M EDTA [pH 8]). Cleavage of transgenic opsin RNA was determined by reverse transcription of all opsin RNA into cDNA and polymerase chain reaction amplification by primers that distinguished the mutant transgene from the normal chromosomal genes. To detect reverse transcription-polymerase chain reaction (RT-PCR) products, [α-$^{32}$P] deoxyadenosine triphosphate was included during the final PCR cycle. The fragments were analyzed by electrophoresis on 4% or 5% nondenaturing polyacrylamide gels. Radioactivity of product, substrate, and ribozyme bands, or of PCR fragments was quantitated by scintillation counting of excised bands or by radio-analytic scanning (Phosphorlmager; Molecular Dynamics, Durham, N.C.).

Kinetic Analysis.

Analyses to determine multiple-turnover kinetic constants were carried out in 20 mM MgCl$_2$, 40 mM Tris-HCl (pH 7.5), at 37° C. for 15 minutes. Samples were preincubated at 37° C. and reactions were initiated by addition of ribozyme to substrate RNA. Samples contained increasing concentrations of substrate RNA, holding ribozyme concentration constant. Values for maximum velocity ($V_{max}$), $K_M$, and $k_{cap}$ were obtained by double reciprocal plots of velocity versus substrate concentration.

Reverse Transcription-Polymerase Chain Reaction (RT-PCR).

RNAs were subjected to reverse transcription using a first strand synthesis kit (Pharmacia: Uppsala, Sweden) primed by oligo-deoxythymidine. The P23H, S334Ter, and wild-type opsin cDNAs were amplified by PCR, using a three-primer system (the downstream primer anneals to the mutant and wild-type cDNAs; two upstream primers anneal to the mutant or wild-type cDNAs) resulting in PCR products of different lengths. Because the mutant transgene was derived from the mouse rhodopsin gene, wild-type (rat) mRNA was distinguished from mutant (mouse) mRNA. The P23H product was 195 nucleotides, the P23 wild-type product was 208 nucleotides, the S334Ter product was 298 nucleotides, and the S334 wild-type product was 315 nucleotides.

The downstream P23H primer (for mutant and wild-type genes) was 5'-CAGCCACGGC CAAGTTGAG (SEQ ID NO. 11). The upstream P23H primer was 5'-GCGTGGGTCG GAGTCACTTC (SEQ ID NO. 12). The upstream P23 primer for wild-type genes was 5'-TCCAACATCA CGGGCGTGGT (SEQ ID NO. 13). The downstream S334Ter primer (for mutant and wild-type genes) was 5'-TGGGGAGCCTCATTTTG (SEQ ID NO. 14). The upstream S334Ter primer was 5'-CTCTTCCATCTATAACCCGG (SEQ ID NO. 15). The upstream S334 primer for wild-type genes was 5'-TTTCTTTGCT AAGACCGCC (SEQ ID NO. 16).

In all control reactions without active ribozyme, the ratio of mutant to wild-type transcript was relatively invariant, 60.6±3.2% for S334TER and 56.5±1.2% for P23H. Because the appropriate combination of mutant and wild-type upstream primers was used for RT-PCR analysis of each transgenic retina, this baseline value reflects a combination of the true mutant:wild-type transcript ratio and any inherent difference in amplification efficiency caused by the two distinct upstream primers. Therefore, any change in this ratio when the ribozyme is added documents an internally corrected measure of allele-specific, ribozyme-mediated RNA cleavage.

EXAMPLE 5

Ribozyme Destruction of an mRNA Causing Retinitis Pigmentosis

Figure 7B:
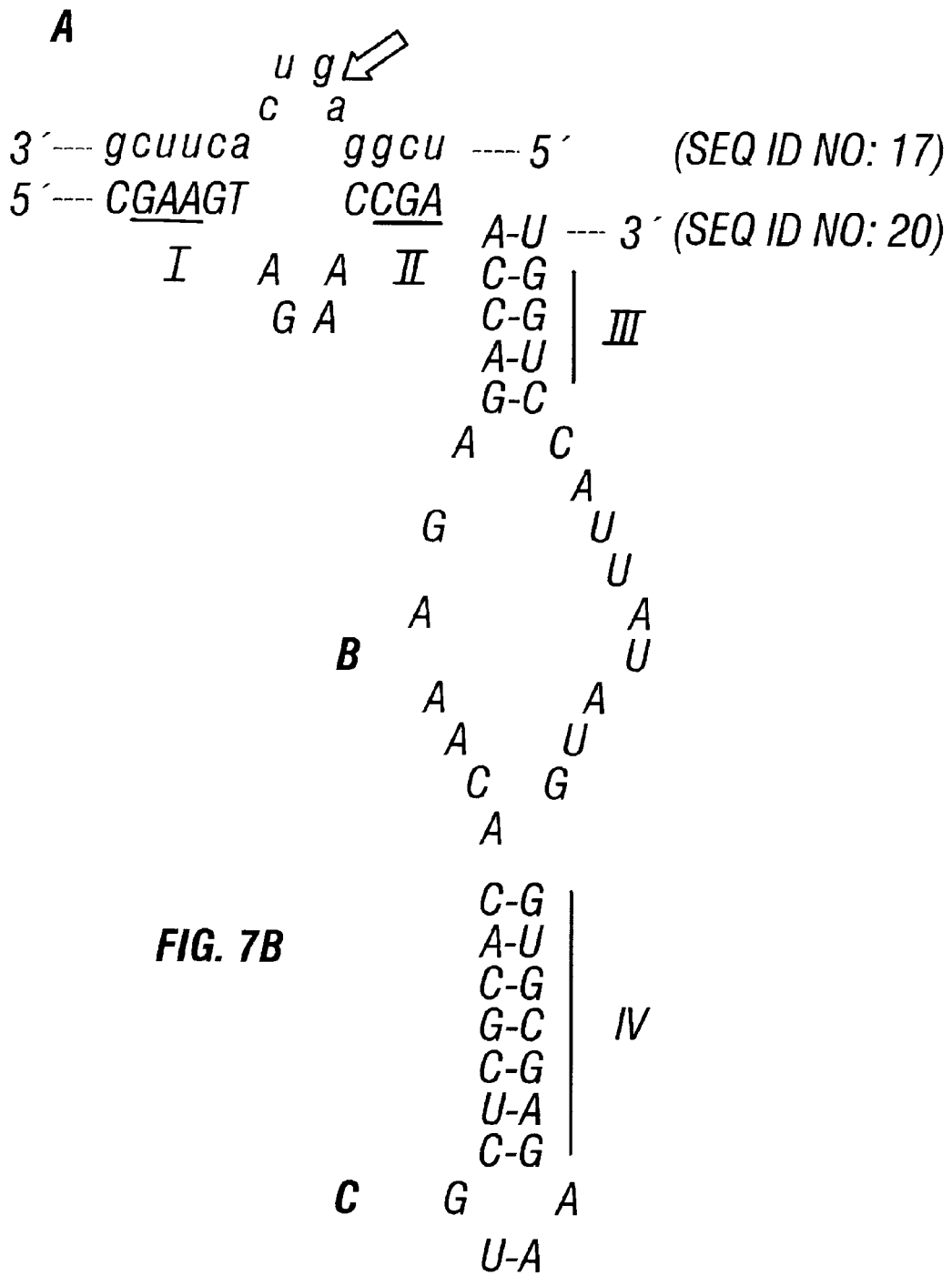

To test the activity and specificity of ribozymes as a tool for combating autosomal dominant retinitis pigmentosa, two hammerhead ribozymes were designed, one targeting the C to A transversion leading to the P23H mutation (P23H-Hh) and the other targeting a UCA to UAA sequence change at codon 334 (S334Ter-Hh; FIG. 7A). Both transgenes contain 2 nucleotide changes relative to the wild-type (rat) sequences in the targeted regions. In the case of P23H, these changes are a C to A transversion in codon 23 and a silent transition mutation in codon 22 (AGC-AGT). The S334termutation was created by altering codon 334 from TCC to TAA. A hairpin ribozyme was also created to cleave the P23H mRNA (P23H-Hp) at the same sequence as the hammerhead (FIG. 7B). These modifications were tested to determine the most active structure in vitro. The U39:C mutation increased cleavage activity two-fold compared with that in the naturally occurring hairpin structure, and the extension of helix IV to 9 base pairs, capped by a GUAA tetraloop, increased cleavage activity fourfold. The effect of these changes were not additive in the double mutant, however. We also strengthened helix II of the hammerhead ribozyme compared with that of the naturally occurring structure by substituting G:C base pairs for A:T pairs (FIG. 7A).

Using these activity-increasing modifications, three ribozymes were tested for sequence specificity of cleavage. In addition to the three active ribozymes, corresponding inactive ribozymes were used as a control for antisense effects. These inactive ribozymes contained mutations at residues known to be critical in the catalytic activity of the hairpin and hammerhead ribozymes.

For each active ribozyme, the cleavage reaction resulted in two discrete products: a larger 5' fragment and a smaller 3' fragment, which resulted from the breakage of the targeted phosphodiester bond. In the case of P23H-Hh and P23H-Hp the 5' products were 26 and 29 nucleotides, respectively. For the S334Ter hammerhead ribozyme, the 5' product was 39 nucleotides and the 3' product was 18 nucleotides. The S334Ter-Hh ribozyme appeared less active than did the ribozymes directed against the P23H target.

No cleavage products were detected after incubation of the active ribozymes with the wild-type opsin target RNAs. The cleavage site in the P23H and S334Ter (mutant) targets differ in two nucleotide positions from their respective wild-type sequences. Similarly, there was no digestion of a target after incubation with the inactive ribozymes. This result confirms that appearance of the smaller band depends on the catalytic domains.

EXAMPLE 6

Cleavage is Dependent on Magnesium Concentration

Because of the key role of $Mg^{2+}$ in RNA structure and in the breakage of phosphodiester bonds, the cleavage assay was performed with each of the ribozymes as a function of magnesium concentration. Although all the ribozymes showed greater activity in higher concentrations of magnesium, the greatest increase was seen between 0 mM and 20 mM. Improvement of cleavage reached a plateau at 80 mM magnesium, but little difference was seen beyond that point. All ribozymes cleaved at magnesium concentrations of 5 mM or less, indicating that cleavage will occur under physiological conditions.

EXAMPLE 7

Ribozymes Target and Cleave Intact Retinal RNA

Although the active ribozymes specifically cleaved synthetic target RNAs, an important question relevant to their application in vivo is whether they exhibit similar specificity on full-length mRNA in the context of all RNAs found in retinal photoreceptors. These ribozymes were assayed using total RNA isolated from the retinas of transgenic rats. These Sprague-Dawley rats contain the P23H mutant rhodopsin transgene or the S334Ter mutant rhodopsin transgene, in addition to their normal endogenous rhodopsin alleles. Both mutant transgenes were derived from the mouse rod opsin gene. The retinal RNA extracts were used as target substrates in place of the synthetic targets in the standard ribozyme cleavage assay to test the activity of the ribozymes against full-length mRNA. In this case, RT-PCR was used to detect the wild-type and mutant targets. Cleavage of the mutant mRNA derived from the transgene should reduce the level of this RT-PCR product compared with that derived from the endogenous (wild-type) gene.

The active ribozymes specifically cleaved the transgenic opsin RNA molecules during an extended (12-hour) incubation. The relative concentrations of mutant and wild-type mRNA was determined by RT-PCR analysis specific for the two messages. In the S334Ter transgenic rats, the mutant mRNA was deterined by RT-PCR analysis specific for the two messages. In the S334Ter transgenic rats, the mutant mRNA was 60.6% that of wild-type opsin mRNA before treatment. After incubation with S334Ter-Hh ribozyme, the amount of transgenic RNA was reduced by 17% compared with that of the wild-type. A more dramatic drop was observed when the hammerhead ribozyme was directed against the P23H animals; the mutant transgene was expressed at 56.5% of the wild-type level. After incubation with P23H-Hh, the level was reduced by approximately 50%. The hairpin ribozyme cleaved the P23H RNA to a lesser extent, resulting in a reduction of 19% compared with that of the wild-type standard. Thus, these ribozymes bind and cleave their respective targets, effectively distinguishing among the cellular mRNAs.

EXAMPLE 8

Construction of Vectors and Expression in Target Cells rAAV-ribozyme Constructs.

Recombinant AAV constructs were based on the pTR-UF2 vector (Zolotukhin, S., M. Potter, W. W. Hauswirth et al. [1996] *J. Virol.* 70:4646– 4654). They resemble the vector used by Flannery et al. (Flannery, J. G., S. Zolotukhin, M. I. Vaquero et al. [1997] *Proc. Natl. Acad. Sci. USA* 94:6916–6921) to direct GFP expression to rat photoreceptors except that a 691 bp fragment of the proximal bovine rod opsin promoter replaced the 472 bp murine rod opsin promoter and the ribozyme gene replaced the gfp gene. The bovine promoter fragment contains three proximal promoter elements and the endogenous transcriptional start site at its 3' end (DesJardin, L. E., W. W. Hauswirth [1996] *Inv. Ophth. Vis. Sci.* 37:154–165) and supports high efficiency, rat photoreceptor-specific expression in vivo. Active and inactive ribozymes were designed, tested and cloned as described above. Each ribozyme gene was followed by an internally cleaving hairpin ribozyme derived from plasmid pHC (Altschuler, M., R. Tritz, A. A. Hampel [1992] *Gene* 122:85–90) resulting in ribozyme cassettes of 140–152 bp. Self cleavage at the internal cutting site in the primary ribozyme RNA leaves identical 3' ends on each mature ribozyme. The ribozyme cassette was preceded by an intron derived from SV40 and followed by a polyadenylation signal in order to promote nuclear export of the ribozyme. Recombinant AAV titers were determined using both an infectious center assay (Flannery, J. G., Zolotukhin, S. Vaquero et al. [1997] *Proc. Natl. Acad. Sci. USA* 94:6916–6921) and a DNAse resistant physical particle assay employing a quantitative, competitive PCR of the neor gene contained within all rAAV-ribozyme particles (Zolotukhin, S., M. Potter, W. W. Hauswirth et al. [1996] *J. Virol.* 70:4646–4654). Each of the four rAAV-ribozyme virus preparations contained $10^{10}$ to $10^{11}$ DNASE resistant particles per ml and $10^8$ to $10^9$ infectious center units per ml. Contaminating helper adenovirus and wild-type AAV, assayed by serial dilution cytopathic effect or infectious center assay respectively, were less than five order of magnitude lower than rAAV.

Subretinal Injection of rAAV.

Line 3 albino transgenic rats (P23H-3) on an albino Sprague-Dawley background (produced by Chrysalis DNX Transgenic Sciences, Princeton, N.J.) were injected at the ages of P14 or P15. Animals were anesthetized by ketamine/xylazine injection, and a direction, and b-waves were measured from the cornea-negative peak to the major cornea-positive peak. For quantitative comparison of differences between the two eyes of rats, the values from all the stimulus intensities were averaged for a given animal.

Retinal Tissue Analysis.

The rats were euthanized by overdose of carbon dioxide inhalation and immediately perfused intracardially with a mixture of mixed aldehydes (2% formaldehyde and 2.5% glutaraldehyde). Eyes were removed and embedded in epoxy resin, and 1 $\mu$m thick histological sections were made along the vertical meridian. Tissue sections were aligned so that the ROS and Müller cell processes crossing the inner plexiform layer were continuous throughout the plane of section to assure that the sections were not oblique, and the thickness of the ONL and lengths of RIS and ROS were measured as described by Faktorovich et al. (Faktorovich, E. G., R. H. Steinberg, D. Yasamura et al. [1990] *Nature* 347:83–86). Briefly, 54 measurements of each layer or structure were made at set points around the entire retinal section. These data were either averaged to provide a single value for the retina, or plotted as a distribution of thickness or length across the retina. The greatest 3 contiguous values for ONL thickness in each retina were also compared to determine if any region of retina (e.g., nearest the injection site) showed proportionally greater rescue; although most of these values were slightly greater than the overall mean of all 54 values, they were no different from control values than the overall mean. Thus, the overall mean was used in the data cited, since it was based on a much larger number of measurements.

RT-PCR.

For quantification of opsin mRNA retina from ribozyme injected or control eyes, retina were isolated without fixation and total RNA immediately extracted using the RNeasy Minikit (Qiagen, Santa Clarita, Calif.). RT-PCR was performed using the Pharmacia First-Strand cDNA synthesis kit employing oligo dT as the primer. Wild-type and transgene opsin cDNAs were amplified using a three primer system described above. Primers specific for β-actin cDNA (Timmers, A. M., B. R. Newton, W. W. Hauswirth [1993] *Exp. Eye Res*. 56:251–265) were included in each reaction for internal standardization.

Such constructs result in persistent photoreceptor expression of the passenger gene of greater than 15 months. Ribozymes were designed to recognize and cleave the unique transcript produced by the P23H transgene. The mutant target sequence "5'-UCGGAGUCACUUCG-3'" (SEQ ID NO. 17) contains two differences from the wild-type mRNA (indicated in bold). The hairpin ribozyme (Hp11) cleaved 3' to the first adenosine residue (underlined) and the hammerhead ribozyme (Hh13) cleaved 3' to the central cytosine residue (underlined). Control ribozymes (Hp11i and Hh13i, respectively) retained the targeting domains but contained fatal flaws in their catalytic domains. In vitro, the active hammerhead ribozyme (Hh13) was able to cleave 20% of the P23H target within 10 min. of incubation and by 5 hours greater than 80% was converted to the expected products. In multiturnover experiments, both ribozymes exhibited kinetic constants ($K_m$ and $k_{cat}$) similar to those of naturally occurring ribozymes. The two active ribozymes produced negligible cleavage of the wild-type transcript even in the presence of high $MgCl_2$ concentrations. Control ribozymes (Hp11i and Hh13i) containing inactivating mutations in their catalytic domains were without measurable activity on any substrate. Using total RNA derived from retinas of P23H rats on P62, both the hairpin and the hammerhead ribozymes were able to cleave the mRNA product of the mutant transgene selectively.

For experiments in vivo, a line of transgenic rats, TgN (P23H)3 (abbreviated P23H-3), that has a retinal degeneration phenotype similar to patients with retinitis pigmentosa (Steinberg, R. H., J. G. Flannery, M. I. Naash et al. [1996] *Inv. Ophth. Vis. Sci*. 37:S698) was used. Expression of the mutated opsin transgene begins at about postnatal day (P) 5 in rats, leading to a gradual death of photoreceptor cells. These rats develop an apparently normal retina up to P15, although there are somewhat more pyknotic photoreceptor nuclei in the outer nuclear layer (ONL) than in non-transgenic control rats. Thereafter, death of photoreceptor cells is almost linear until about P60, resulting in loss of about 40% of the photoreceptors. After P60, the rate of cell loss decreases, until by one year the retinas have less than a single row of photoreceptor nuclei. The rAAV-ribozymevector was injected into the interphotoreceptor space between the photoreceptors and the adjacent retinal pigment epithelium at P14 or P15. Rats were sacrificed and eyes examined at 3 time points between P60–P90. At these ages in uninjected control eyes of P23H-3 rats, the ONL thickness, which is an index of photoreceptor cells number, was reduced to about 60% of normal.

Ribozyme-injected eyes showed a modest but significant decrease in the accumulation of transcript derived from the P23H transgene. Control eyes exhibited little variation in the level of transgene opsin mRNA. Eyes injected with either active ribozyme uniformly exhibited lowered transgene mRNA levels relative to total opsin mRNA in the same eye. Retinas receiving the hairpin ribozyme Hp11 showed a 15.3±3.3% decrease in transgene expression, and those with the hammerhead ribozyme Hh13 showed a decrease of 11.1±5.1% decrease.

Histologically, eyes injected with the ribozymes retained significantly more photoreceptors at P60, P75 and P90 than uninjected contralateral control eyes. Retinas receiving a subretinal injection of Hh13 at P14–15 retained 88% of the normal ONL thickness, compared to about 60% in the uninjected controls (FIG. 8a). Thus, the ONL thickness after Hh13 expression was 40–43% greater than that of uninjected P23H-3 controls (FIG. 8b), a highly significant difference (p=0.001 or less at P60 and P90). Injection of the Hp11 ribozyme also resulted in significant rescue when compared to controls, with preservation of 77–83% of normal ONL thickness (FIG. 8a). Thus, the ONL thickness after Hp11 expression was 30–39% greater than that of uninjected P23H-3 controls (FIG. 8b), a highly significant difference (p<0.0005 at all ages).

There was little or no rescue in PBS-injected control eyes (p>0.169 in all cases) as shown in FIG. 8a. As a control for possible rescue by the expression of the bovine opsin promoter (BOPS), AAV-BOPS-gfp was injected at a titer of $1.75 \times 10^8$, similar to the titer used with the AAV-ribozymes. The injection of AAV-BOPS-gfp did not rescue photoreceptors (FIG. 8a). The inactive Hp11i did yield ONL thickness measures greater than uninjected control values, but they were consistently less than that resulting from the active Hp11 and Hh13 ribozymes (FIG. 8a).

The pan-retinal extent of photoreceptor rescue that resulted from a single 2-μl injection of the rAAV suspension was surprising (FIG. 8b). From photoreceptor counts, it is estimated that there are approximately $10^7$ photoreceptors in the rat retina. Recombinant AAV titers were estimated using both an infectious center assay and a physical particle assay. Together they permit construction of upper and lower bounds for the number of functional rAAV particles in a single 2 μl injection. The upper bound derives from the DNAse resistant particle assay, indicating that 2 μl of the rAAV-ribozyme virus preparation contained $2 \times 10^7$ to $10^8$ rAAV. This is an upper bound because not all particles counted are expected to be infectious. The lower bound for rAAV titer is generated by the infectious center assay, indicating $10^6$ to $10^7$ rAAV per μl.

The lateral extent of rescue resulting from a single injection may also be explained by the unique nature of the retinal tissue. For in vivo delivery to the photoreceptors, rAAV is injected into extracellular space separating the photoreceptor and retinal pigment epithelium (RPE) layers. The initial volume of extracellular space, approximately 0.5 μl, increases greatly with the 2 μl injection. Following injection, the fluid transport function of the RPE dehydrates this space, reapposing the photoreceptors and RPE and concentrating the rAAV. The detachment of the photoreceptors from the RPE resolves within several hours. During the reattachment process, viral particles are spread laterally through the subretinal space.

Along with the survival of more photoreceptor cells, injection of the ribozymes resulted in greater lengths of rod inner segments (RIS) and rod outer segments (ROS). In the case of RIS, the uninjected control retinas had RIS that were about 90% of normal. Both the active and inactive ribozymes resulted in RIS lengths of 98% or greater of the normal length, and about 10–15% longer than uninjected controls. The PBS and AAV-BOPS-gfp were indistinguishable from uninjected eyes. The ROS lengths were about 15–25% longer in the ribozyme-injectedeyes compared to those in the uninjected control eyes. However, ROS in the ribozyme-injected eyes were, at greatest, only 65–75% of normal, compared to the virtually normal RIS lengths. The ROS of the active ribozymes differed significantly from the uninjected controls ($p<0.005$ for all, except $<0.02$ for Hp11 at P90), as did the inactive Hp11i ($p<0.05$).

The finding that ribozyme-targeteddestruction of P23H mutant RNA markedly slows the rate of retinal degeneration in P23H transgenic rats, along with functional preservation of the retina, is the first demonstration of this therapeutic approach in an animal model of a dominantly inherited human disease. Furthermore, because complete removal of mutant rRNA is not necessary to achieve phenotypic rescue, this approach can be applied to other dominantly inherited diseases as well.

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING

```
<160> NUMBER OF SEQ ID NOS: 23

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 1
gccctgcagg acgacgccta agccaccgct tccggatccg gc                          42

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 2
gccctgcagg gtcggagtca cttcgagcag ggatccggc                              39

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 3
gccctgcagg acgacgcctc tgccaccgct tccggatccg gc                          42

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 4
gccctgcagg gtcggagccc cttcgagcag ggatccggc                              39

<210> SEQ ID NO 5
<211> LENGTH: 34
<212> TYPE: DNA
```

<213> ORGANISM: Artificial Sequence
<220> FEATURE:
<223> OTHER INFORMATION: Description of Artificial Sequence:SYNTHETIC OLIGONUCLEOTIDE

<400> SEQUENCE: 5
gcgcggtacc gtggctctga tgagccgctt cggc     34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:SYNTHETIC OLIGONUCLEOTIDE

<400> SEQUENCE: 6
gcgcacgcgt gacgcctttc gccgccgaag cggc     34

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:SYNTHETIC OLIGONUCLEOTIDE

<400> SEQUENCE: 7
gcgcggtacc cgaagtctga tgagccgctt cggc     34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:SYNTHETIC OLIGONUCLEOTIDE

<400> SEQUENCE: 8
gcgcacgcgt tcggagtttc gccgccgaag cggc     34

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:SYNTHETIC OLIGONUCLEOTIDE

<400> SEQUENCE: 9
gcgcggtacc gaagtagaac cgaaccagag aaaca     35

<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence:SYNTHETIC OLIGONUCLEOTIDE

<400> SEQUENCE: 10
gcgcacgcgt accaggtaat ataccacgct cttacgagcg tgtgtttctc tggtt     55

<210> SEQ ID NO 11
<211> LENGTH: 19
<212> TYPE: DNA
<213> ORGANISM: Artificial Sequence

```
<220> FEATURE:
<223> OTHER INFORMATION: Description of Artificial Sequence:SYNTHETIC
      OLIGONUCLEOTIDE

<400> SEQUENCE: 11
cagccacggc caagttgag                                                        19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 12
gcgtgggtcg gagtcacttc                                                       20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 13
tccaacatca cgggcgtggt                                                       20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 14
tggggagcct cattttg                                                          17

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 15
ctcttccatc tataacccgg                                                       20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 16
tttctttgct aagaccgcc                                                        19

<210> SEQ ID NO 17
<211> LENGTH: 14
<212> TYPE: RNA
<213> ORGANISM: Artificial Sequence
<220> FEATURE:
```

<223> OTHER INFORMATION: Description of Artificial Sequence:SYNTHETIC
      OLIGONUCLEOTIDE

<400> SEQUENCE: 17
ucggagucac uucg                                                           14

<210> SEQ ID NO 18
<211> LENGTH: 14
<212> TYPE: RNA
<213> ORGANISM: Artificial Sequence
<220> FEATURE:
<223> OTHER INFORMATION: Description of Artificial Sequence:SYNTHETIC
      OLIGONUCLEOTIDE

<400> SEQUENCE: 18
gacgccuaag ccac                                                           14

<210> SEQ ID NO 19
<211> LENGTH: 37
<212> TYPE: RNA
<213> ORGANISM: Artificial Sequence
<220> FEATURE:
<223> OTHER INFORMATION: Description of Artificial Sequence:SYNTHETIC
      RIBOZYME

<400> SEQUENCE: 19
guggcucuga ugagccgcuu cggcggcgaa aggcguc                                  37

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence:SYNTHETIC
      RIBOZYME

<400> SEQUENCE: 20
cgaagtagaa ccgaaccaga gaaacacacg cucguaagag cgugguauau uaccuggu          58

<210> SEQ ID NO 21
<211> LENGTH: 37
<212> TYPE: RNA
<213> ORGANISM: Artificial Sequence
<220> FEATURE:
<223> OTHER INFORMATION: Description of Artificial Sequence:SYNTHETIC
      RIBOZYME

<400> SEQUENCE: 21
cgaagucuga ugagccgcuu cggcggcgaa acuccga                                  37

<210> SEQ ID NO 22
<211> LENGTH: 13
<212> TYPE: RNA
<213> ORGANISM: Artificial Sequence
<220> FEATURE:
<223> OTHER INFORMATION: Description of Artificial Sequence:SYNTHETIC
      RIBOZYME

<400> SEQUENCE: 22
ccacuucgag uac                                                            13

<210> SEQ ID NO 23
<211> LENGTH: 36
<212> TYPE: RNA
<213> ORGANISM: Artificial Sequence
<220> FEATURE:
<223> OTHER INFORMATION: Description of Artificial Sequence:SYNTHETIC -continued

```
        RIBOZYME

<400> SEQUENCE: 23
guacuccuga ugagccgcuu cggcggcgaa aagugg                        36
```

What is clamed is:

1. A ribozyme that specifically cleaves an mRNA encoding a mutant rod opsin polypeptide in a retinal cell of a mammalian eye.

2. The ribozyme of claim 1, wherein said ribozyme specifically cleaves an mRNA encoding a mutant rod opsin polypeptide that comprises a P23H mutation.

3. The ribozyrne of claim 1, wherein said ribozyme specifically cleaves an mRNA encoding a mutant rod opsin polypeptide that comprises an S334Ter mutation.

4. The ribozyme of claim 1, wherein said ribozyme comprises a sequence selected from the group consisting of SEQ ID NO:19, SEQ ID NO:20, SEQ ID NO:21, and SEQ ID NO:23.

5. The ribozyme of claim 4, wherein said ribozyme comprises the sequence of SEQ ID NO:19.

6. The ribozyme of claim 4, wherein said ribozyme comprises the sequence of SEQ ID NO:20.

7. The ribozyme of claim 4, wherein said ribozyme comprises the sequence of SEQ ID NO:21.

8. The ribozyme of claim 4, wherein said ribozyme comprises the sequence of SEQ ID NO:23.

9. A catalytic RNA molecule that specifically cleaves an mRNA encoding a mutant rod opsin polypeptide in a retinal cell of a mammal.

10. The catalytic RNA molecule of claim 9, wherein said molecule is a hammerhead ribozyme.

11. The catalytic RNA molecule of claim 9, wherein said molecule is a hairpin ribozyme.

12. A vector comprising a polynucleotide encoding a ribozyme that specifically cleaves an mRNA encoding a mutant rod opsin polypeptide, said polynucleotide operably linked to at least a first regulatory element that directs expression of said polynucleotide in a mammalian cell.

13. The vector of claim 12, wherein said vector is a viral vector.

14. The vector of claim 13, wherein said viral vector is an adeno-associated viral vector.

15. The vector of claim 12, wherein said ribozyme selectively cleaves an mRNA that encodes a mutant rod opsin polypeptide comprising a P23H or an S334Ter mutation.

16. The vector of claim 15, wherein said ribozyine comprises a sequence selected from the group consisting of SEQ ID NO:19, SEQ ID NO:20, SEQ ID NO:21, and SEQ ID NO:23.

17. The vector of claim 12, wherein said regulatory element directs expression of said polynucleotide in a retinal cell.

18. The vector of claim 12, wherein said regulatory element comprises a mammalian rod opsin promoter element.

19. An adeno-associated viral vector comprising a polynucleotide that encodes a ribozyme that specifically cleaves an mRNA encoding a mutant rod opsin polypeptide.

20. The adeno-associated viral vector of claim 19, wherein said ribozyme specifically cleaves an mRNA encoding a mutant rod opsin polypeptide comprising the P23H or S334Ter mutation.

21. The adeno-associated viral vector of claim 20, wherein said ribozyme comprises a sequence selected from the group consisting of SEQ ID NO:19, SEQ ID NO:20, SEQ ID NO:21, and SEQ ID NO:23.

22. The adeno-associated viral vector of claim 19, wherein said polynucleotide is operably linked to at least a first regulatory element that directs expression of said polynucleotide in a mammalian cell.

23. The adeno-associated viral vector of claim 19, wherein said regulatory element comprises a mammalian rod opsin promoter element.

24. A host cell that comprises:
   (a) a ribozyme that specifically cleaves an mRNA encoding a mutant rod opsin polypeptide;
   (b) a catalytic RNA molecule that specifically cleaves an mRNA encoding a mutant rod opsin polypeptide;
   (c) a vector comprising a polynucleotide that encodes a ribozyme that specifically cleaves an mRNA encoding a mutant rod opsin polypeptide; or
   (d) an adeno-associated viral vector comprising a polynucleotide that encodes a ribozyme that specifically cleaves an mRNA encoding a mutant rod opsin polypeptide.

25. The host cell of claim 24, wherein said cell is a mammalian host cell.

26. The host cell of claim 25, wherein said mammalian host cell is a human cell.

27. The host cell of claim 26, wherein said human cell is a retinal cell.

28. The host cell of claim 27, wherein said retinal cell is a photoreceptor cell.

29. The host cell of claim 28, wherein said retinal cell is a photoreceptor rod or cone cell.

30. A composition comprising:
   (a) a ribozyme or a catalytic RNA molecule that specifically cleaves an mRNA encoding a mutant rod opsin polypeptide in a retinal cell of a mammalian eye;
   (b) a vector or an adeno-associated viral vector comprising a polynucleotide encoding a ribozyme that specifically cleaves an mRNA encoding a mutant rod opsin polypeptide, said polynucleotide operably linked to at least a first regulatory element that directs expression of said polynucleotide in a mammalian cell; or
   (c) a host cell that comprises:
      (i) a ribozyme or a catalytic RNA molecule that specifically cleaves an mRNA encoding a mutant rod opsin polypeptide; or
      (ii) a vector or an adeno-associated viral vector that comprises a polynucleotide encoding a ribozyme that specifically cleaves an mRNA encoding a mutant rod opsin polypeptide.

31. The composition of claim 30, further comprising a pharmaceutical excipient.

32. The composition of claim 31, wherein said pharmaceutical excipient is suitable for ocular or subretinal administration.

33. The composition of claim 30, further comprising a liposome.

34. A kit comprising the ribozyme of claim 38, and instructions for using said kit.

35. A kit comprising the catalytic RNA molecule of claim 9, and instructions for using said kit.

36. A kit comprising the vector of claim 12 or claim 19, and instructions for using said kit.

37. A kit comprising the host cell of claim 24, and instructions for using said kit.

38. A kit comprising the composition of claim 30, and instructions for using said kit.

39. A method for decreasing the amount of mRNA encoding a mutant rod opsin polypeptide in a retinal cell of a mammalian eye, comprising directly administering to said eye an amount of (a) the ribozyme of claim 1, (b) the molecule of claim 9, (c) the vector of claim 12 or claim 19, or (d) the composition of claim 30, effective to specifically cleave said mRNA in said cell.

40. The method of claim 39, wherein said ribozyme specifically cleaves an mRNA encoding a rod opsin polypeptide that comprises the P23H mutation.

41. The method of claim 39, wherein said ribozyme specifically cleaves an mRNA encoding a rod opsin polypeptide that comprises the S334Ter mutation.

42. The method of claim 39, wherein said ribozyme comprises a sequence selected from the group consisting of SEQ ID NO:19, SEQ ID NO:20, SEQ ID NO:21, and SEQ ID NO:23.

43. The method of claim 42, wherein said ribozyme comprises the sequence of SEQ ID NO:19.

44. The method of claim 42, wherein said ribozyme comprises the sequence of SEQ ID NO:20.

45. The method of claim 42, wherein said ribozyme comprises the sequence of SEQ ID NO:21.

46. The method of claim 42, wherein said ribozyme comprises the sequence of SEQ ID NO:23.

47. The method of claim 42, wherein said retinal cell is a photoreceptor cell.

48. The method of claim 42, wherein directly administering comprises ocular or subretinal injection.

49. The method of claim 42, wherein said method is used in the treatment or amelioration of a pathological condition that results from the expression of said mutant rod opsin polypeptide in said retinal cell.

50. The method of claim 49, wherein said pathological condition is retinal degeneration, retinitis, or macular degeneration.

51. The method of claim 50, wherein said retinitis is retinitis pigmentosa.

52. The method of claim 51, wherein said pathological condition is autosomal dominant retinitis pigmentosa or autosomal recessive retinitis pigmentosa.

53. The method of claim 50, wherein said pathological condition is macular degeneration.

54. The method of claim 53, wherein said pathological condition is age-related macular degeneration.

55. A method for decreasing the amount of mRNA encoding a mutant rod opsin polypeptide in a retinal cell of a mammalian eye, comprising directly administering to said eye an amount of (a) the ribozyme of claim 1, or (b) the catalytic RNA molecule of claim 9, effective to specifically cleave said mRNA in said cell.

56. A method for decreasing the amount of mRNA encoding a mutant rod opsin polypeptide in a retinal cell of a mammalian eye, comprising directly administering to said eye an amount of (a) the vector of claim 12 or (b) the vector of claim 19, effective to specifically cleave said mRNA in said cell.

57. A method for decreasing the amount of mutant rod opsin polypeptide in the eye of a mammal suspected of having a pathological condition selected from the group consisting of retinal degeneration, retinitis, and macular degeneration, comprising directly administering to said eye an amount of (a) the ribozyme of claim 1, (b) the molecule of claim 9, (c) the vector of claim 12 or claim 19, or (d) the composition of claim 30, effective to specifically cleave mRNA encoding said polypeptide, and thereby decreasing the amount of said polypeptide in said eye.

58. A method for treating a pathological condition that results from the expression of a mutant rod opsin polypeptide in a retinal cell of a mammalian eye, said method comprising directly administering to said mammalian eye an amount of (a) the ribozyme of claim 1, (b) the molecule of claim 9, (c) the vector of claim 12 or claim 19, or (d) the composition of claim 30, effective to treat said pathological condition.

59. The method of claim 58, wherein said pathological condition is selected from the group consisting of retinal degeneration, retinitis, and macular degeneration.

60. A method for ameliorating the symptoms of a pathological condition of a mammalian eye, comprising directly administering to said eye an amount of (a) the ribozyme of claim 1, (b) the molecule of claim 9, (c) the vector of claim 12 or claim 19, or (d) the composition of claim 30, effective to ameliorate said symptoms of said pathological condition.

61. The method of claim 60, wherein said symptoms are selected from the group consisting of atrophic lesions of the eye, pigmented lesions of the eye, blindness, a reduction in peripheral vision and a reduction in central vision.

62. A method for reducing the progression of a pathological condition of the eye, comprising directly administering to said eye an amount of (a) the ribozyrne of claim 1, (b) the molecule of claim 9, (c) the vector of claim 12 or claim 19, or (d) the composition of claim 30, effective to reduce the progression of said pathological condition.

* * * * *

UNITED STATES PATENT AND TRADEMARK OFFICE
CERTIFICATE OF CORRECTION

PATENT NO. : 6,225,291 B1
DATED : May 1, 2001
INVENTOR(S) : Alfred S. Lewin, William W. Hauswirth and Kimberly Drenser It is certified that error appears in the above-identified patent and that said Letters Patent is hereby corrected as shown below:

Column 28, claim 23,
Line 18, delete "19" and insert therefor -- 22 --.

Column 29, claim 34,
Line 1, delete "38" and insert therefor -- 1 --.

Column 29, claim 47,
Line 36, delete "42" and insert therefor -- 39 --.

Column 29, claim 48,
Line 38, delete "42" and insert therefor -- 39 --.

Column 29, claim 49,
Line 40, delete "42" and insert therefor -- 39 --.

Column 30, claim 57,
Line 20, after "(b) the" insert -- catalytic RNA --.

Column 30, claim 58,
Line 30, after "(b) the" insert -- catalytic RNA --.

Column 30, claim 59,
Line 35, delete "and macular degeneration" and insert therefor -- macular generation, and retinopathy --.

Signed and Sealed this

Twenty-ninth Day of January, 2002

*Attest:*

*Attesting Officer*

JAMES E. ROGAN
*Director of the United States Patent and Trademark Office*